US011800990B2

(12) United States Patent
White et al.

(10) Patent No.: US 11,800,990 B2
(45) Date of Patent: Oct. 31, 2023

(54) PERFUSION ASSESSMENT USING TRANSMISSION LASER SPECKLE IMAGING

(71) Applicant: Covidien AG, Neuhausen am Rheinfall (CH)

(72) Inventors: Sean Michael White, Santa Ana, CA (US); Bruce Yee Yang, Irvine, CA (US); Tyler Bywaters Rice, Santa Ana, CA (US)

(73) Assignee: Covidien AG, Neuhausen am Rheinfall (CH)

( * ) Notice: Subject to any disclaimer, the term of this patent is extended or adjusted under 35 U.S.C. 154(b) by 1122 days.

(21) Appl. No.: 15/850,391

(22) Filed: Dec. 21, 2017

(65) Prior Publication Data

US 2018/0199829 A1 Jul. 19, 2018

Related U.S. Application Data

(63) Continuation of application No. 13/762,316, filed on Feb. 7, 2013, now Pat. No. 9,848,787.

(Continued)

(51) Int. Cl.
*A61B 5/026* (2006.01)
*A61B 5/00* (2006.01)

(52) U.S. Cl.
CPC .......... *A61B 5/0261* (2013.01); *A61B 5/6826* (2013.01); *A61B 2562/0238* (2013.01)

(58) Field of Classification Search
CPC ................ A61B 5/0261; A61B 5/6826; A61B 2562/0238
See application file for complete search history.

(56) References Cited

U.S. PATENT DOCUMENTS

| 5,372,136 A | 12/1994 | Steuer et al. |
| 5,499,627 A | 3/1996 | Steuer et al. |

(Continued)

FOREIGN PATENT DOCUMENTS

| WO | WO-2010096453 A1 * | 8/2010 | .......... A61B 5/0059 |
| WO | WO 2015/176294 | 11/2015 | |

OTHER PUBLICATIONS

Kirkpatrick, S., et al. "Detrimental effects of speckle-pixel size matching in laser speckle contrast imaging," Optics Letters. vol. 33(24), 2008. p. 2886-2888 (Year: 2008).*

(Continued)

*Primary Examiner* — Christopher Koharski
*Assistant Examiner* — Sean A Frith
(74) *Attorney, Agent, or Firm* — Shumaker & Sieffert, P.A.

(57) ABSTRACT

Methods and apparatus for measuring perfusion using transmission laser speckle imaging are provided. The apparatus comprises a coherent light source and a detector configured to measure transmitted light associated with an unfocused image at one or more locations. The coherent light source and detector are positioned in a transmission geometry. The apparatus further comprises means for securing the coherent light source and the detector to the tissue sample in a fixed transmission geometry relative to the tissue sample. The apparatus may further comprise at least one processor to receive information from the detector and process detected variations in transmitted light intensity to determine a single metric of perfusion. The method may comprise the steps transilluminating a tissue sample with coherent light, recording spatial and/or temporal variations in the transmitted light signal, determining speckle contrast value(s), and computing a metric of perfusion.

23 Claims, 14 Drawing Sheets

Related U.S. Application Data

(60) Provisional application No. 61/596,168, filed on Feb. 7, 2012.

(56) References Cited

U.S. PATENT DOCUMENTS

| | | | | |
|---|---|---|---|---|
| 6,253,097 | B1* | 6/2001 | Aronow | A61B 5/14552 600/310 |
| 7,113,817 | B1* | 9/2006 | Winchester, Jr. | A61B 3/1233 356/27 |
| 2002/0095075 | A1 | 7/2002 | Madarasz et al. | |
| 2004/0127779 | A1 | 7/2004 | Steuer et al. | |
| 2004/0220480 | A1 | 11/2004 | Braeuer et al. | |
| 2005/0043606 | A1* | 2/2005 | Pewzner | A61B 5/1455 600/407 |
| 2005/0089243 | A1 | 4/2005 | Ludwig | |
| 2005/0143662 | A1 | 6/2005 | Marchitto et al. | |
| 2006/0281992 | A1* | 12/2006 | Stothers | A61B 5/208 600/438 |
| 2008/0183059 | A1 | 7/2008 | LaPlante et al. | |
| 2008/0188726 | A1 | 8/2008 | Presura et al. | |
| 2008/0188728 | A1 | 8/2008 | Neumann et al. | |
| 2008/0200786 | A1* | 8/2008 | Berndsen | A61B 5/6838 600/344 |
| 2008/0234590 | A1 | 9/2008 | Akkermans et al. | |
| 2009/0118623 | A1* | 5/2009 | Serov | A61B 5/0261 600/476 |
| 2009/0256949 | A1* | 10/2009 | Rana | G02B 23/14 348/340 |
| 2010/0026995 | A1* | 2/2010 | Merritt | A61B 5/1455 356/222 |
| 2010/0155577 | A1 | 6/2010 | Kiesel et al. | |
| 2010/0168585 | A1 | 7/2010 | Fujii et al. | |
| 2010/0286497 | A1* | 11/2010 | Fine | A61B 5/0261 600/504 |
| 2011/0013002 | A1* | 1/2011 | Thompson | A61B 5/0261 348/77 |
| 2011/0026783 | A1 | 2/2011 | Fujii et al. | |
| 2012/0071769 | A1 | 3/2012 | Dunn et al. | |
| 2012/0095354 | A1 | 4/2012 | Dunn et al. | |
| 2012/0130215 | A1 | 5/2012 | Fine et al. | |
| 2012/0130257 | A1* | 5/2012 | Heanue | A61B 5/0071 600/476 |
| 2012/0162438 | A1 | 6/2012 | Thakor et al. | |
| 2012/0232363 | A1 | 9/2012 | Al-Ali et al. | |
| 2012/0301839 | A1* | 11/2012 | Stoianovici | A61B 5/0088 433/27 |
| 2014/0049779 | A1 | 2/2014 | Tin et al. | |
| 2014/0206976 | A1 | 7/2014 | Thompson et al. | |

OTHER PUBLICATIONS

Boas et al., "Laser speckle contrast imaging in biomedical optics," Journal of Biomedical Optics, 011109, Jan.-Feb. 2010, vol. 15 (1), 12 pp.

Cannesson et al., "Does the Pleth Variability Index Indicate the Respiratory-Induced Variation in the Plethysmogram and Arterial Pressure Waveforms?," Anesthesia & Analgesia, vol. 106, No. 4, Apr. 2008, 6 pp.

Choi et al., "Linear response range characterization and in vivo application of laser speckle imaging of blood flow dynamics," Journal of Biomedical Optics 11 (4), 041129, published online Aug. 31, 2006, 7 pp.

Fercher et al., "Flow Visualization by Means of Single-Exposure Speckle Photography," Optics Communications, vol. 37, No. 5, Jun. 1, 1981, 5 pp.

Flock et al., "Optical Properties of Intralipid: A Phantom Medium for Light Propagation Studies," Lasers in Surgery and Medicine, 1992, 10 pp.

Jakobsson et al., "Prediction of sampling depth and photon pathlength in laser Doppler flowmetry," Medical & Biological Engineering & Computing, May 1993, 7 pp.

Killip III "Oscillation of blood flow and vascular resistance during Mayer waves." Circulation research, vol. XI, Dec. 1962, 7 pp.

Kirkpatrick et al., "Detrimental effects of speckle-pixel size matching in laser speckle contrast imaging," Optics Letters, Optical Society of America, vol. 33, No. 24, Dec. 15, 2008, 4 pp.

Prosecution History from U.S. Appl. No. 13/762,316, dated Apr. 28, 2015 through Aug. 16, 2017, 169 pp.

Qiu et al., "Spatiotemporal laser speckle contrast analysis for blood flow imaging with maximized speckle contrast," Journal of Biomedical Optics 15 (1), published online Jan. 15, 2010, 5 pp.

Ramirez-San-Juan et al., "Impact of velocity distribution assumption on simplified laser speckle imaging equation," Optical Society of America, published Feb. 22, 2008, vol. 16, No. 5, 7 pp.

White et al., "Automated computation of functional vascular density using laser speckle imaging in a rodent window chamber model," available onlie Mar. 17, 2011, retrieved from http://choi.bli.uci.edu/files/2013/11/MVR_2011_82_92.pdf, 5 pp.

Yuan et al., "Determination of optimal exposure time for imaging of blood flow changes with laser speckle contrast imaging," Applied Optics, Apr. 1, 2005, vol. 44, No. 10, Optical Society of America, 8 pp.

Dunn et al., "A Transmissive Laser Speckle Imaging Technique for Measuring Deep Tissue Blood Flow: An Example Application in Finger Joints," Lasers in Surgery and Medicine, vol. 43, Jan. 15, 2011, pp. 21-28.

International Search Report and Written Opinion of International Application No. PCT/US17/25979, dated Jun. 21, 2017, 9 pp.

International Search Report and Written Opinion of International Application No. PCT/US2018/041398, dated Jul. 13, 2017, 12 pp.

* cited by examiner

PERFUSION ASSESSMENT USING TRANSMISSION LASER SPECKLE IMAGING

CROSS-REFERENCE TO RELATED APPLICATIONS

This application is a continuation of U.S. application Ser. No. 13/762,316, filed Feb. 7, 2013, which claims priority from U.S. Provisional Application No. 61/596,168, filed Feb. 7, 2012, both of which are incorporated herein by reference and should be considered a part of this specification.

BACKGROUND

Field

Disclosed herein are systems and methods for measuring perfusion and blood flow. More particularly, a system is disclosed using laser speckle imaging in a transmission geometry to measure perfusion and blood flow.

Description of the Related Art

Many situations exist where the perfusion of tissues with blood is correlated to the health and/or physical state of an individual. For example, during traumatic injuries, a potentially worsening prognosis is indicated by transient peripheral limb ischemia (e.g., decreased blood flow to peripheral limb tissues). In this case, blood is preferentially collected within the vital organs of the body. A clinician can typically only visually recognize signs of this event by observing the onset of cyanosis. However, cyanosis only becomes visible at blood oxygenation levels far below normal physiologic levels (~<80%). As such, devices and methods for quantitatively measuring and reporting the degree of perfusion and the strength of blood flow within peripheral limbs before the onset of cyanosis would aid clinicians in treating patients in critical condition earlier than would be possible based on visual assessment. In addition, peripheral limb perfusion has been demonstrated as an indicator of the onset of general and epidural anesthesia, infectious outcomes in neonates and infants, and restriction and/or restoration of blood flow during surgical procedures. Peripheral perfusion measurements may also provide diagnostic or prognostic information in individuals with peripheral vascular disorders.

Pulse oximetry is a common method for clinical assessment of pulse rate, blood oxygenation, and perfusion. This method relies on the changes in light absorption resulting from the pulsatile flow of arterial blood. Currently, pulse oximeters do not measure perfusion directly, but rely instead on other measured parameters that may be correlated with perfusion. They also require a pulsatile beat to determine these parameters. As a result, the functionality of pulse oximeters to measure perfusion is compromised under conditions such as ischemia, low cardiac output, or the use of extracorporeal means to provide blood flow. These conditions can result in pulse oximeters giving erroneous information, or no information at all. Thus pulse oximeters fail to deliver information that could be integral to proactively treating patients with potentially decreased blood flow.

Another method for assessment of perfusion uses a laser Doppler flowmeter. Laser Doppler flowmeters only interrogate tissue ~1 mm deep with respect to the surface of the tissue. Such a small depth of interrogation may result in sampling only superficial blood vessels when used on human patients. This would limit the data acquired from larger arteries, arterioles, veins, and venules, which may provide more valuable perfusion information.

Further, conventional laser Doppler flowmeters used for point measurement on patients utilize an optical fiber to transfer light to and from the probe. Movements of this optical fiber result in erroneous changes in reported perfusion values. As such, patient movement can have significant deleterious effects on acquired perfusion data.

Additionally, typical laser Doppler flowmeters cost tens of thousands of dollars. This high cost significantly limits the availability of such devices to a fairly limited number of applications and precludes using such devices in the majority of emergency rooms, surgical suits, ambulances, or disaster or battlefield triage sites, etc.

SUMMARY OF THE INVENTION

An apparatus for measuring tissue perfusion may comprise a coherent light source and a detector configured to receive one or more pixels associated with an unfocused image of a tissue sample. The coherent light source and the detector are positionable in a transmission geometry with respect to the tissue sample. The apparatus my further comprise an enclosure configured to accommodate the tissue sample. The enclosure may be coupled to the coherent light source and the detector. The enclosure may comprise a clam shell configuration. The tissue sample may be a finger, toe, nostril, or earlobe. The apparatus my further comprise an opaque sheet positioned between the detector and the tissue sample, wherein the opaque sheet is configured to adjust an aperture of the detector. The detector may be a photodiode.

An apparatus for measuring tissue perfusion may comprise a coherent light source and a detector configured to receive one or more pixels associated with an image of a tissue sample. The apparatus my further comprise a means for securing the coherent light source and the detector to the tissue sample in a fixed transmission geometry relative to the tissue sample, such that movement of the tissue sample while measuring tissue perfusion does not alter the transmission geometry. A field of view of the tissue sample may remain constant upon movement of the tissue sample. The means for securing may comprise an enclosure configured to securely accommodate the tissue sample. The enclosure may be coupled to the coherent light source and the detector. The enclosure may comprise a clam shell configuration. The tissue sample may be a finger, toe, nostril, or earlobe. The apparatus may further comprise an opaque sheet positioned between the detector and the tissue sample, wherein the opaque sheet is configured to adjust an aperture of the detector.

A method of measuring perfusion in a region of tissue may comprise receiving, by a processor, a plurality of light intensity values from a detector. The plurality of light intensity values may be associated with transilluminating a tissue sample with a coherent light source rendering an unfocused image. The method may further comprise computing, by the processor, a speckle contrast parameter based at least in part on the plurality of light intensity values. The method may further comprise determining, by the processor, a single metric of perfusion based at least in on the computed speckle contrast parameter. The method may further comprise displaying, by the processor, the determined single metric of perfusion. The plurality of light intensity values received by the detector may remain constant upon movement of the tissue sample. The tissue sample may be a finger, toe, nostril, or earlobe. The method may further comprise calculating a standard deviation across the unfocused entire image.

DETAILED DESCRIPTION

Figure 1:
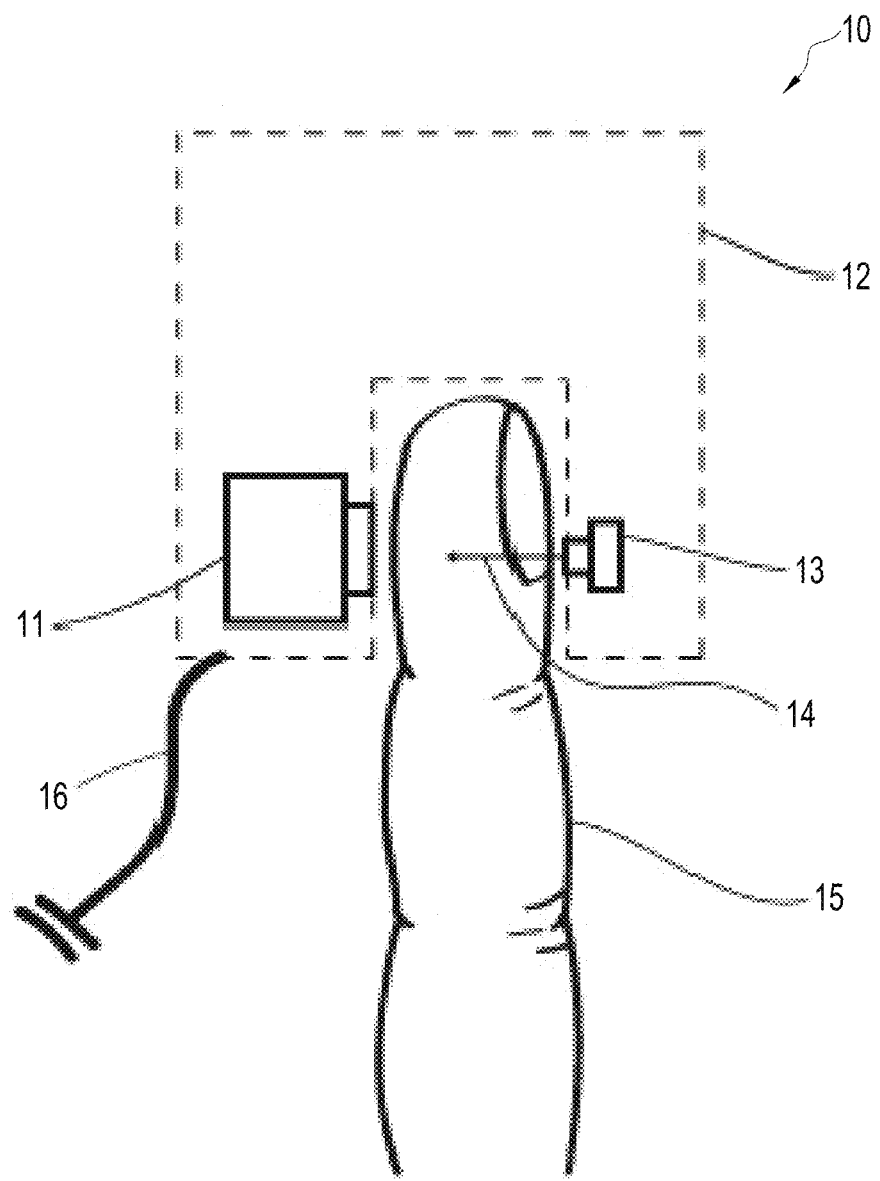
FIG. 1 illustrates one embodiment of the invention configured to measure perfusion in a human finger.
Figure 2:
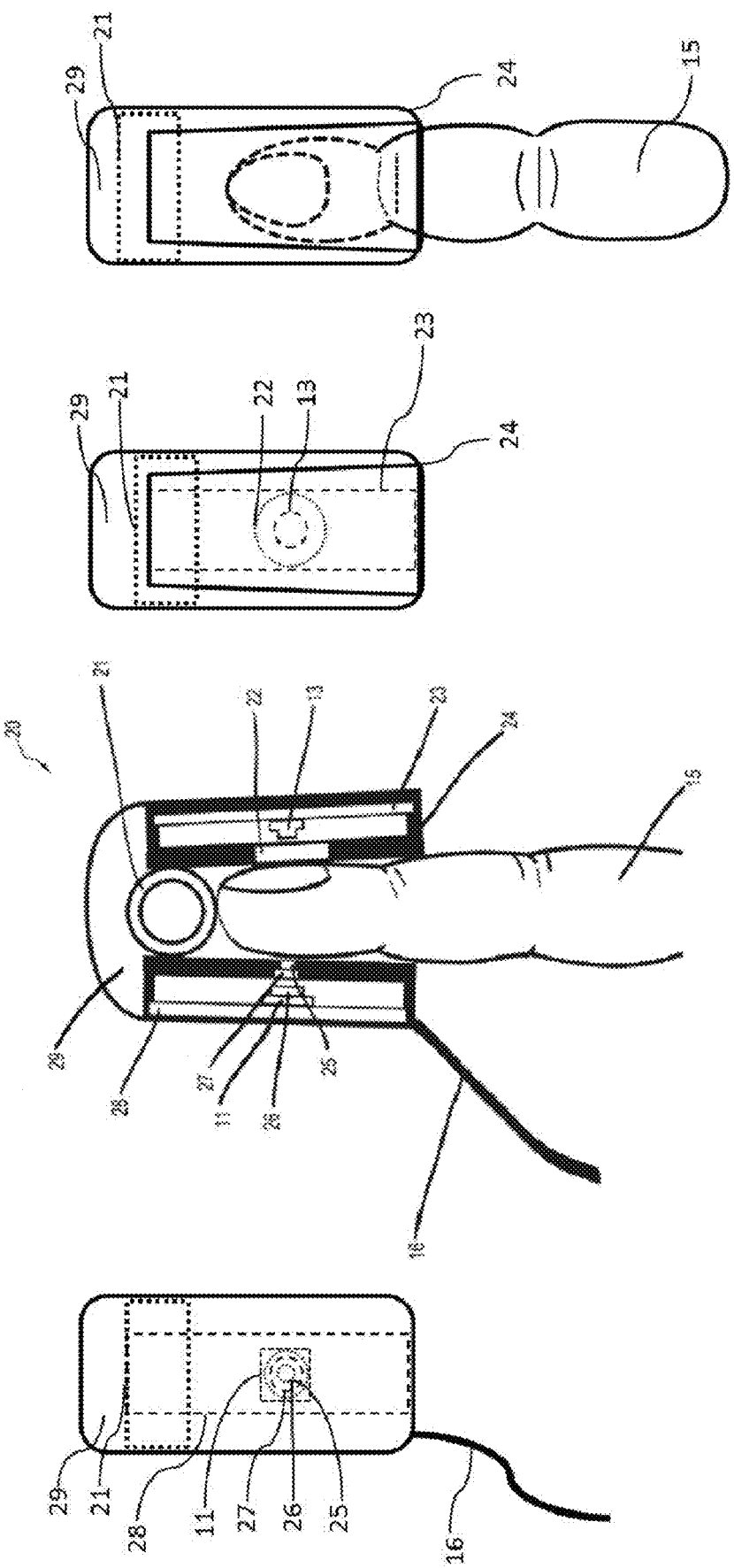
FIGS. 2a-d illustrate perspective views of another embodiment of the invention configured to measure perfusion in a human finger.

An apparatus and methodology to measure perfusion using laser speckle imaging ("LSI") are disclosed. The apparatus and methodology may make use of a finger, toe, earlobe, nostril, or any other suitable tissue as a site of measurement.

Laser speckle imaging ("LSI") is an imaging methodology used to create image-based representations of blood flow in tissues of interest. LSI illuminates a part of a patient's body, e.g., a finger or toe, using coherent light. The presence and movement of blood within the illuminated body part interacts with the light moving through the tissue. Thus, coherent laser light is scattered within samples of interest. These scattering events lead to a difference in path length among photons. The result is a speckle pattern that is typically imaged using a detector, such as a camera with a finite exposure time. If the scattering objects (such as blood cells) are in motion, the speckle pattern fluctuates in time and blurs during the camera exposure. The amount of blurring is related to flow and quantified using a parameter called the speckle contrast.

Various features of alteration can be used to extract information about the presence and flow of blood. Such features include changes in detected light intensity and contrast within the observed light pattern, both of which are correlated with the movement of red blood cells. Analysis of changes in intensity and contrast within the observed light pattern over time then provides dynamic and quantitative feedback about alterations in a patient's peripheral blood flow and tissue perfusion, from which informed inferences may be made with respect to the patient's physical state. Because it has been shown that this information can be acquired under circumstances where pulse oximeters (the current gold standard for analysis of patient hemodynamics) no longer function adequately, LSI provides information to clinicians that is vital to the proactive treatment of critically ill patients.

Perfusion information provided by the disclosed LSI systems is comparable to information provided by a laser Doppler flowmeter, but a LSI system can be built from commercially available parts at a fraction of the cost. The cost of a laser Doppler flowmeter can be as much as two orders of magnitude higher than the cost of the disclosed LSI systems. Besides cost, the disclosed LSI systems provide several other advantages, including the ability to interrogate the full thickness of a tissue, compact size, and reduced measurement error caused by movement of the optical fiber used in laser Doppler flowmeters.

Given that LSI is an image-producing methodology, existing LSI systems are designed to achieve an adequate field of view for a variety of objects for a variety of clinical purposes. For example, LSI is used for clinical measurements such as cranial blood flow, retinal blood flow, and burn-wound blood flow. Given these applications, the size of LSI systems must be sufficiently large to maintain an adequate field of view for the object being imaged. In addition, many of the measurements in field of LSI are performed on static samples such as anesthetized and secured animals and static phantoms. Therefore, existing LSI systems do not include the detector and coherent light source in a compact enclosure.

Furthermore, because LSI is an image-producing methodology, LSI systems generate images of perfusion. Thus, narrowing the field of view is disadvantageous. For example, narrowing the field of view presents less data, and would not be applicable to the clinical settings in which LSI is used, such as cranial blood flow, retinal blood flow, and burn-wound blood flow. Additionally, if the field of view is too narrow, there is a risk that the coherent light source will not hit a blood vessel, such that any perfusion data would be inaccurate. Because a compact enclosure containing the coherent light source and detector would significantly narrow the field of view, existing LSI systems are not included in a compact enclosure.

In addition, because existing LSI systems require a focused imaged, existing LSI systems must provide a proper focal length. Thus, the size and configuration of LSI systems are constrained by the necessary focal length. Further, the lens, detector, and other image-forming objects required to maintain a proper focal length add considerable size to existing LSI systems.

The large field of view, focal length, and size associated with existing LSI systems present several limitations. For example, to achieve the proper field of view and focal length, a minimum distance between the laser, detector, and sample must be maintained. This distance poses difficulties in connecting the locations of the detector and/or coherent light source with the tissue sample. Therefore, when a patient moves, the detector and coherent light source remain static. Accordingly, any movement of the tissue being imaged (while the detector and coherent light source remain static) will cause a different field of view to be investigated and may elicit erroneous perfusion values. Thus, if one is interested in monitoring the perfusion in a region over time, the patient, laser, and detector must remain as static as possible. Because even microscopic object movements will produce erroneous perfusion measurements, existing LSI systems are not used in busy emergency or critical care settings.

Accordingly, in some embodiments of the invention, the locations of the coherent light source and detector are coupled to the movement of the tissue sample. As such, patient movement causes the detector and coherent light source to similarly move. Accordingly, the field of view of the tissue sample does not change upon movement of the tissue sample. The coupling of the detector, coherent light source, and tissue sample may be facilitated by shortening the distance between the detector and coherent light source. The distance between the detector and coherent light source may be shortened by reducing the field of view and forgoing the formation of a focused image, thereby eliminating the need for a focal length. In some embodiments, the coherent light source and detector are included in a compact enclosure, such as a clam shell. The clam shell may be configured to accommodate a tissue sample, such as a finger.

Even though LSI is an imaging methodology, some embodiments of the invention reduce the field of view to observe, for example, only a portion of a finger. The viewable area of tissue may be reduced due to the close proximity of the detector, object, and coherent light source, according to some embodiments of the invention. For example, in some embodiments, the detector and coherent light source are included in a compact clam shell that can be clipped onto a patient's finger. The accuracy of perfusion data is not compromised by reducing the viewable area of tissue, because some embodiments of the invention present perfusion data as a single metric, rather than an image. The single metric of perfusion, as compared to an image, is more easily understood and processed by a user. In addition, narrowing the field of view may present inaccurate data because it decreases the chances that the coherent light source will hit a blood vessel. Accordingly, some embodiments of the invention include the coherent light source and detector in a transmission geometry, which allows for more complete signal acquisition compared to reflection geometry.

Thus, in some embodiments of the invention, the coherent light source and detector move along with the patient as the patient moves. As a result, measurement error due to patient movement is smaller compared to typical LSI systems. Accordingly, the patient is allowed more flexibility to move around while the patient's perfusion measurements are being taken, without compromising the accuracy of the perfusion measurements. In addition, because patient movement generates minimal measurement error, the disclosed LSI systems may be used in busy emergency or critical care settings.

In some embodiments, coherent light is emitted via an optical fiber coupled with a laser source. In these embodiments, the optical fiber may emit a portion of the coherent light emitted by the coherent light source. The location of the coherent light source can be coupled to patient movement by fixing the location of the coherent light source and/or the optical fiber with respect to the tissue sample. As used herein, "coherent light source" shall include coherent light emitted via an optical fiber and/or the coherent light source itself.

Existing LSI systems require the formation of a focused image. Out-of-focus images are generally understood to create erroneous/incomplete perfusion data. For example, out-of-focus images may create speckle sizes that are too small to be properly sampled by the detector. Specifically, the detector may under-sample the speckle pattern intensity values, leading to erroneous data. Thus, existing LSI systems utilize a focused image in order to maintain an adequate speckle size to pixel size ratio and adequately sample the speckle pattern. As another example, out-of-focus speckles translate, which may skew speckle contrast in the direction of translation and create "streaking images." This phenomenon creates distortions and artifacts in the speckle contrast image. Because in-focus speckles fluctuate in place, they do not translate and do not create "streaking images." As another example, out-of-focus images are not able to distinguish between sections of high blood flow from low blood flow, because out-of-focus speckles blur features in the image together. For at least these reasons, existing LSI systems utilize in-focus images.

Requiring the formation of a focused image presents several limitations. For example, existing LSI systems require a lens, system of lenses, or mirrors, which add to the size and cost of such systems. As used herein, "lens" or "lenses" shall refer to a lens, system of lenses, mirror, or any other optical instruments for creating a focused image. In addition, because existing LSI systems require a focused image, the distance between the detector and the coherent light source must provide a sufficient focal distance to enable a focused image. Thus, not only must the lens and detector be carefully chosen for its optical properties, but the distance between the laser, lens, sample, and/or detector must also be carefully chosen in existing LSI systems.

In contrast, some embodiments of the invention do not require the formation of a focused image on the detector. Thus, some embodiments of the invention may forgo lenses, thereby reducing the cost and size compared to existing LSI systems. In addition, existing LSI systems require a detector with image-forming optics, whereas some embodiments of the invention may use a cheaper detector without image-forming optics, such as a photodiode.

Furthermore, removing the requirement for a focal length allows the distance between the laser, sample, and/or detector to be designed with more flexibility. Accordingly, in some embodiments of the invention, the detector and coherent light source are included in a compact enclosure. In some embodiments of the invention, the coherent light source and detector may be placed directly in contact with the sample. The compact enclosure further fixes the location of the detector and coherent light source with respect to the sample, thereby reducing measurement error due to patient movement.

In some embodiments, the detector receives an unfocused image, rather than a focused image. Out-of-focus images have the benefit of being more robust to inhomogeneities. Inhomogeneities are caused by non-uniform illumination, absorption, or scattering inhomogeneities. Inhomogeneities are reflected as sharp light intensity values in in-focus images. As such, calculating speckle contrast from in-focus images can lead to erroneous measurement data. By using out-of-focus images, some embodiments of the invention are more robust with respect to inhomogeneities and display more accurate data.

In some embodiments, the invention includes an opaque sheet with an aperture near the detector. The opaque sheet increases the speckle size incident on the detector, and thus obviates the problem of under-sampling traditionally associated with unfocused images and small speckle sizes. Additionally, some embodiments of the invention calculate perfusion using values using all the pixels in an image, instead of small sliding windows. By doing so, artifacts from streaking images are eliminated. In addition, the fact that the direction of perfusion in fingertips is random also helps to remove artifacts according to some embodiments of the invention.

Another limitation of LSI is the fact that it has been performed in a reflection geometry with the laser and detector on the same side of the tissue of interest. In this setup, laser light incident on the tissue of interest must be reemitted to reach the detector. Because perfusion is based upon the flow of blood and blood is very highly forward scattering, performing LSI in a reflection geometry provides a low signal to noise ratio.

Accordingly, in some embodiments, a coherent light source and a detector are used in a transmission geometry. In a transmission geometry, the coherent light source and the detector are positioned on opposite sides of a tissue of interest. Thus, the detector is configured to receive transmitted light that travels through the entire thickness of the tissue. In contrast, existing LSI systems use a reflection geometry wherein the detector receives backscattered light from the tissue of interest. As mentioned, because blood is very highly forward scattering, the usage of transmitted light rather than backscattered light provides a higher signal to noise ratio. In addition, transmission geometry allows for signal acquisition from all of the blood vessels or the majority of blood vessels within the tissue of interest.

Furthermore, transmission geometry allows the coherent light source to be placed in close proximity to the sample of interest. In some embodiments, the coherent light source contacts the surface of the sample of interest. In LSI, the light must exit from the field of view in order to capture an accurate image. Otherwise, the light will obstruct the object being imaged. However, because the light is transmitted through the sample in a transmission geometry in some embodiments, rather than reflected back, transmission geometry allows the light source to be placed in close proximity to the sample.

Although the embodiments described herein illustrate uses of the invention with a finger, the person of ordinary skill in the art will appreciate that the embodiments can be modified to acquire perfusion data from any suitable tissue site. In some embodiments, the tissue is chosen so that coherent light can travel through the thickness of the tissue and reach the detector. For example, the tissue may be an earlobe, nostril, toe, or any tissue with a relatively short path length. Other tissues may be used as well, given the proper illumination wavelength, power, and detector. Because red blood cells are light scatterers of interest in measuring perfusion, the tissue preferably includes blood vessels according to some embodiments.

Referring to FIG. 1, an enclosure 12 configured to accommodate a finger 15 is illustrated. The enclosure 12 includes a coherent light source 13 and a detector 11 positioned within the enclosure 12 in a transmission geometry. Thus, the coherent light source 13 is configured to transilluminate the entire thickness of the finger 15. Similarly, the detector 11 is configured to receive transmission light 14 after it travels through the entire thickness of the finger 15. A cable 16 may also be provided with the enclosure 12 to transfer data to a processor. Data may be transferred to the processor through any suitable mechanism, such as a wireless, Bluetooth, or Rf mechanism.

As further illustrated in FIG. 1, the locations of the coherent light source 13 and detector 11 are configured to couple to finger movement 15 via an enclosure 12. Accordingly, a patient's moving will cause the coherent light source 13 and detector 11 to move along with the patient's finger 15, according to some embodiments of the invention. Thus, the field of view of the tissue sample 15 remains constant upon movement of the tissue sample. Therefore, movement of the tissue sample 15 while measuring tissue perfusion does not alter the transmission geometry. As used herein, "enclosure" shall refer to any mechanism configured to substantially fix the location of the coherent light source 13, tissue sample 15, and detector 11 in a transmission geometry, and couple the coherent light source 13 and detector 11 to tissue movement 15. For example, "enclosure" may refer to a strap, buckle, elastic band, tape, adhesives, wrap, ribbons, ties, or any other suitable mechanism. In some embodiments, the enclosure may be a cylinder, which is configured to accommodate a finger, such that the tip of the finger is exposed and the remaining part of the finger is covered by the cylinder. The enclosure may also be a box, rectangle, sphere, or any other shape with a similar configuration.

The enclosure 12 significantly reduces the field of view compared to existing LSI systems. Nevertheless, the system according to some embodiments of the invention accurately measure perfusion data.

In some embodiments of the invention, the coherent light source 13 may be chosen to maximize transmission of the light 14 through the tissue of interest 15. For example, the coherent light source 13 may be a laser having a wavelength ranging from 300 nm to 1100 nm. The coherent light source 13 may further be chosen to maximize speckle contrast at the detector 11. The coherent light source 13 may be a single-mode laser diode or a fiber coupled helium-neon laser according to some embodiments. In some embodiments, the coherent light source 13 includes adjustable power output to provide an adequate signal at the detector 11. The detector 11 may be a camera with image-forming optics, such as a charge-coupled device (CCD) camera or a complementary metal-oxide semiconductor (CMOS) camera. Because the invention does not form a focused image according to some embodiments, the detector 11 may also be a camera without image-forming optics, such as a photodiode.

The embodiment illustrated in FIG. 1 does not form a focused image. Therefore, the detector 11 according to some embodiments receives an unfocused image, rather than a focused image. Forgoing a focused image allows components such as lenses or mirrors, which are required to focus an image, to be omitted. Omitting such components allows the size and cost to be reduced. In addition, the distance between the coherent light source 13 and detector 11 may be chosen without regard to any focal length required to form a focused image. This further allows the size to be reduced. In some embodiments, the coherent light source 13 and detector 11 may directly contact the surface of the tissue sample. Reducing the size of the disclosed LSI systems facilitates coupling the detector 11 and coherent light source 13 to tissue movement 15 via, for example, an enclosure 12. Accordingly, the detector 11 and coherent light source 13 move along with the finger 15 when the finger 15 moves.

Referring to FIGS. 2a-d, some embodiments of the invention comprises a compact clam shell 20 that can be clipped onto a patient's finger 15. The clam shell 20 may further include a mechanism for easy deployment and removal. For example, the clam shell 20 may include a spring mechanism 21, hinge, or any other suitable mechanism. The clam shell 20 further comprises an outer shell 24 made of opaque material to reduce any stray light from reaching the detector 11.

As illustrated in FIGS. 2*a-d*, the claim shell 20 fixes the locations of the coherent light source 13, detector 11, and finger 15. Therefore, the locations of the coherent light source 13 and detector 11 are configured to couple to finger movement 15, such that finger movement 15 causes the coherent light source 13 and detector 11 to similarly move as the finger 15 moves. Accordingly, the field of view of the tissue sample 15 does not change upon movement of the tissue sample 15. Thus, movement of the tissue sample while measuring tissue perfusion does not alter the transmission geometry. As a result, finger movement 15 generates minimal measurement error caused by patient movement.

Referring to FIGS. 2*a-d*, the clam shell 20 includes a coherent light source 13 and a detector 11 positioned within the clam shell 20 in a transmission geometry. The clam shell 20 may also include a transparent window 22, an opaque sheet with an aperture 25, a polarizer 26, and an optical filter 27.

The opaque sheet 25 is configured to reduce the numerical aperture of the detector 11. Reducing the numerical aperture of the detector 11 increases speckle size incident on the detector 11, and thus increases speckle contrast. In some embodiments, the opaque sheet 25 is positioned between the detector 11 and the finger 15, so that the opaque sheet 25 receives light that has transilluminated the finger 15.

One or more polarizers 26 are also included in the clam shell 20 according to some embodiments of the invention. Because speckle contrast is increased when all detected light has the same polarization state, the polarizer 26 is positioned to convert light before the light reaches the detector 11 and after it transilluminates the finger 15. Placing the polarizer 26 to convert light before the light enters the finger 15 will not be as effective, because light entering scattering tissue such as a finger 15 becomes depolarized as it is scattered. An optical filter 27 may also be included in the clam shell 20 in order to filter out light not coming from the coherent light source 13.

The clam shell 20 does not include lenses to focus an image. This allows for a compact design of the clam shell 20. A compact design is also achieved because the distance between the coherent light source 13 and detector 15 may be chosen without regard to any focal length required to focus an image.

In use, light from the coherent light source 13 may be transmitted through the optically transparent window 22 and transilluminate the finger 15. The transmitted light is then incident on the opaque sheet with aperture 25, adjusting the numerical aperture of the detector 11 and thus the speckle contrast. The light is then incident upon the optical filter 27, which rejects light other than that from the coherent light source 13. The light is then incident on the polarizer 26 used to increase speckle contrast. The light is then incident on the detector 11. Scattering objects in the finger 15 (such as blood cells) scatter the coherent laser light, resulting in a speckle pattern. Data may then be sent to a processor via a cable 16.

Figure 3:
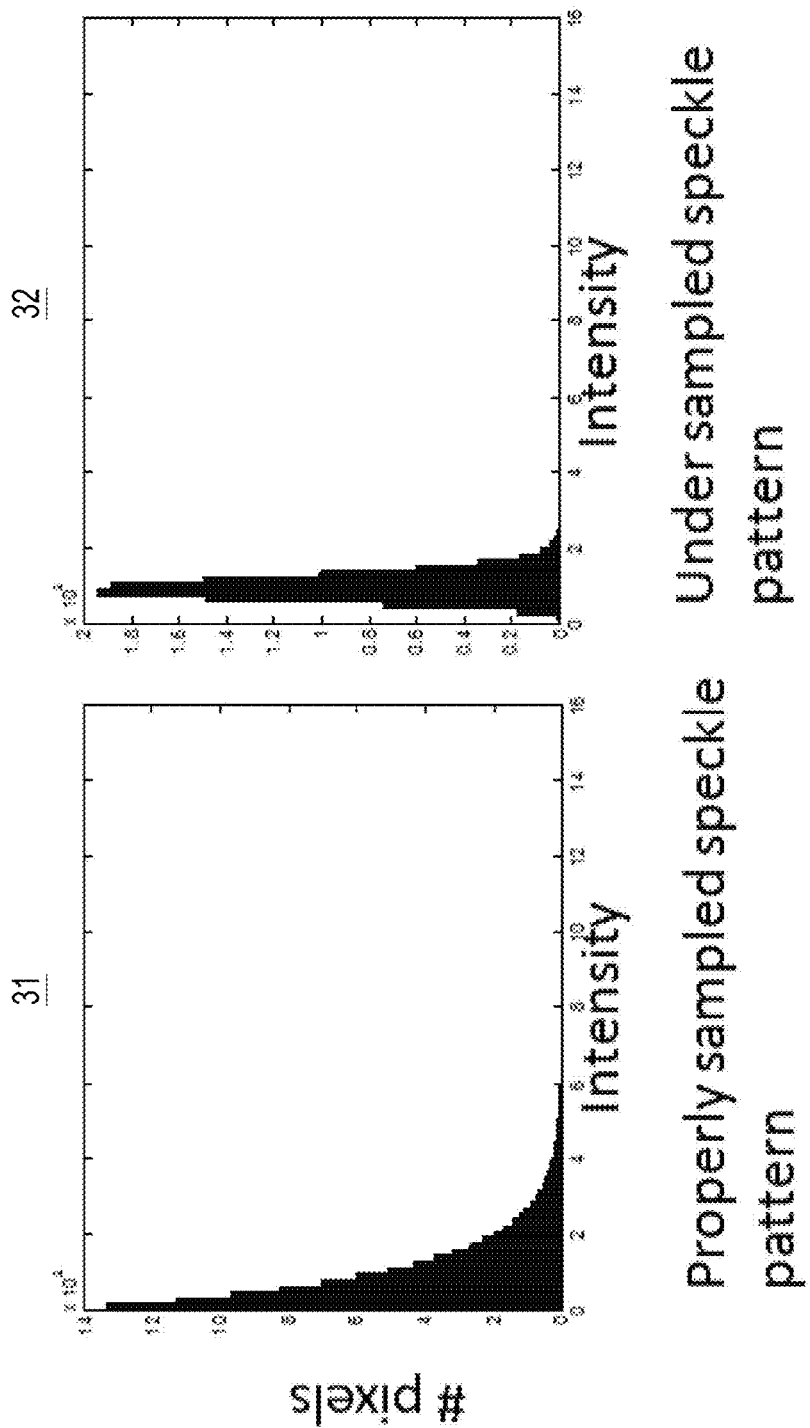
FIG. 3 illustrates histograms of intensities of speckle images.

In the path just illustrated, the light does not travel through any lenses to focus an image. Thus, the image received by the detector 11 is unfocused. Unfocused images may lead to inadequate sampling due to small speckle size, as illustrated in FIG. 3. FIG. 3 illustrates histograms of a properly sampled speckle pattern 31 and an under-sampled speckle pattern 32. As FIG. 3 illustrates, an under-sampled speckle pattern 32 can lead to erroneous data. Nevertheless, the embodiment illustrated in FIGS. 2*a-d* adequately samples speckle contrast, such that perfusion data is accurate. For example, the clam shell 20 illustrated in FIGS. 2*a-d* includes an opaque sheet with an aperture 25 to adjust the numerical aperture of the detector 11. Doing so increases the speckle size incident on the detector 11, and hence, leads to adequate sampling.

Referring to FIGS. 2*a-d*, electronic circuitry is provided through circuit boards, 23, 28, according to some embodiments of the invention. The circuit boards 23, 28 may provide power to the coherent light source 13 as well as any feedback electronics. In some embodiments, the clam shell 20 includes a housing 29, which may be used for additional hardware such as an independent power source, memory, or wireless transmission equipment.

Figure 4A:
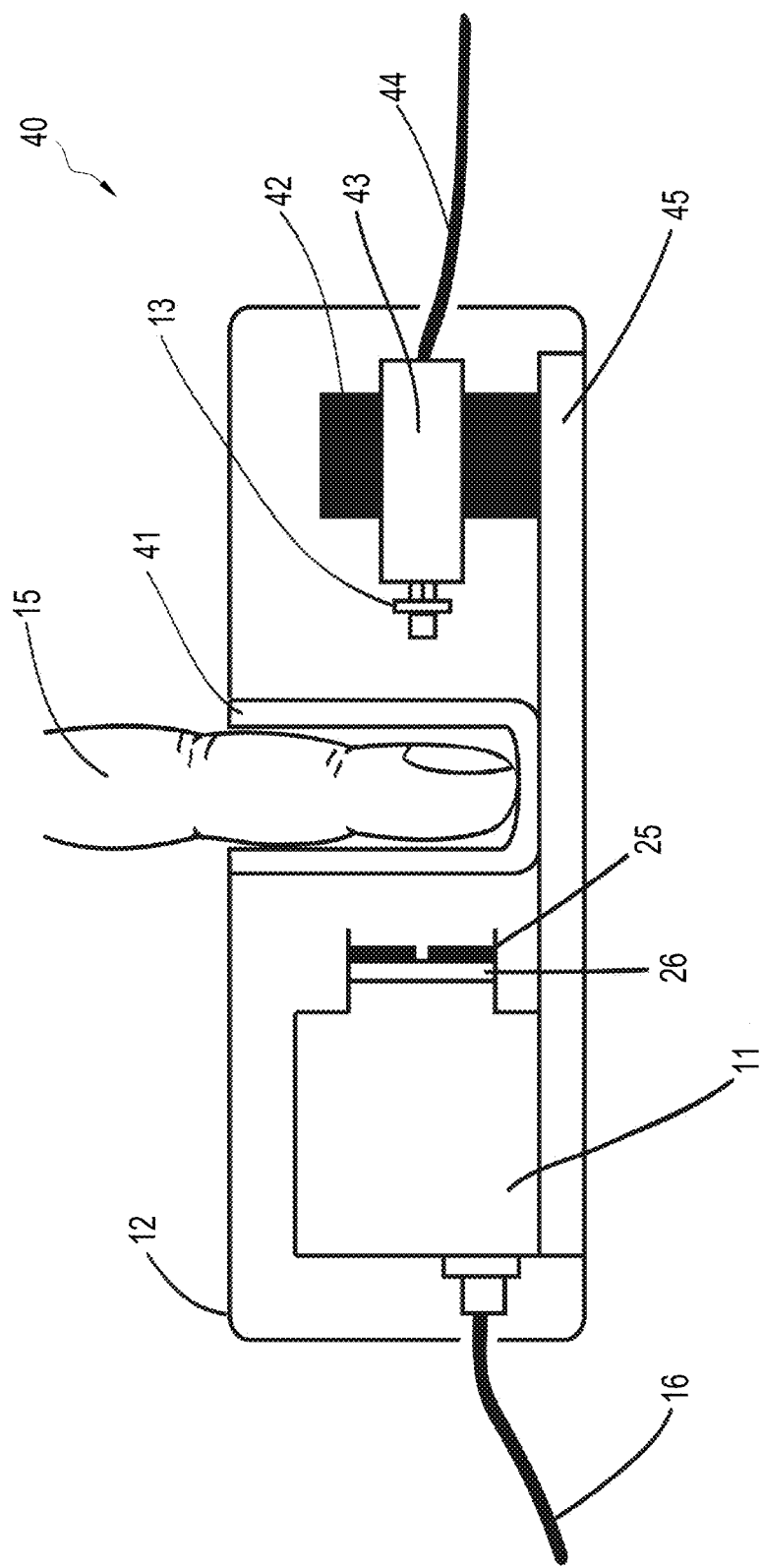
FIG. 4a illustrates another embodiment of the invention configured to measure perfusion in a human finger.
Figure 4B:
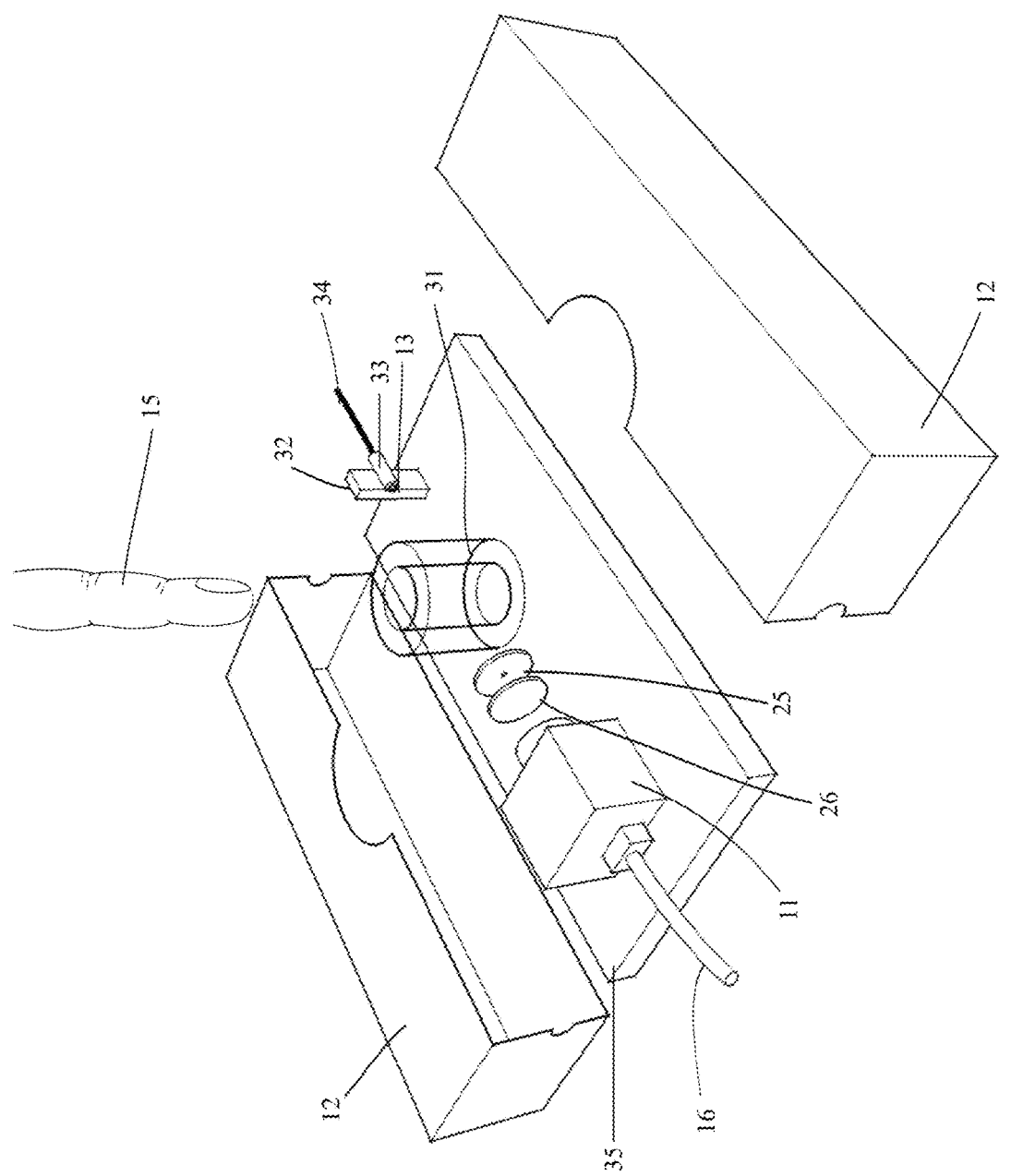
FIG. 4b illustrates an exploded view of another embodiment configured to measure perfusion in a human finger.

FIGS. 4*a-b* illustrates another embodiment of an apparatus 40 for measuring perfusion. Referring to FIGS. 4-*ab*, an enclosure 12 includes a finger cavity 41 configured to accommodate a finger 15. The apparatus further includes a coherent light source 13 mounted to a steel pole 32, a detector 11, an opaque sheet with an aperture 25, and a polarizer 26. The position of the coherent light source 13, finger 15, opaque sheet 25, polarizer 26 and detector 11 is similar to FIGS. 2*a-d*. Thus, light emitted from the coherent light source 13 is first incident on the finger 15, and is scattered by red blood cells in the finger. The light transilluminates the finger 15, then is incident on the opaque sheet 25, then the polarizer 26, and then the detector 11. Components to focus an image, such as lenses, are not included. Thus, the detector 11 receives an unfocused image. However, the opaque sheet 25 increases the speckle size incident on the detector 15. In addition, the locations of the coherent light source 13 and detector 11 are configured to couple to finger movement 15, such that finger movement 15 causes the detector 11 and coherent light source 13 to similarly move. Accordingly, the field of view of the tissue sample 15 does not change upon movement of the tissue sample. Therefore, movement of the tissue sample while measuring tissue perfusion does not alter the transmission geometry. As a result, any measurement error due to patient movement is reduced.

Referring to FIGS. 4*a-b*, the finger cavity 41, steel pole 42, and detector 11 may be mounted to a steel plate 45 for rigidity. In some embodiments, the enclosure 40 is made of an opaque material to reduce stray light reaching the detector 11. Power may be supplied to the coherent light source 13 via a cable 44 connected to a jack 43. Data may be transferred from the detector 11 to a processor via a cable 16.

Figure 5:
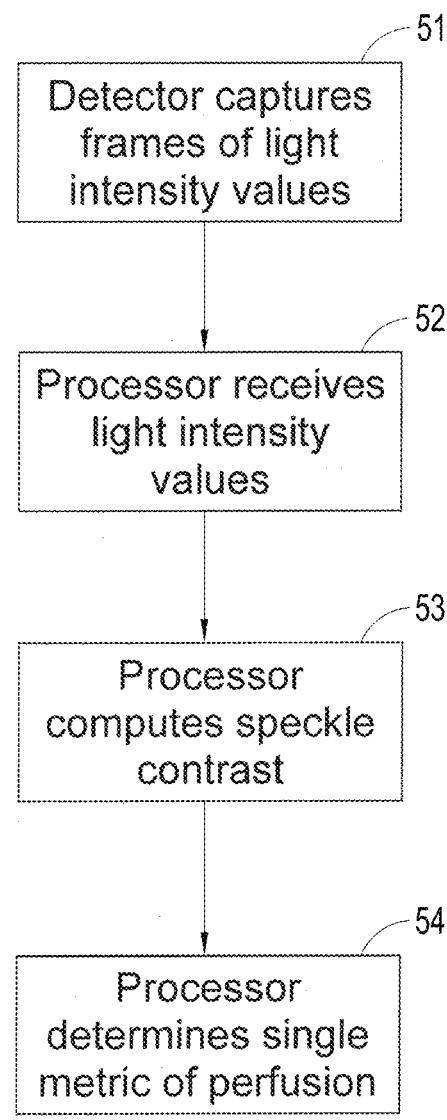
FIG. 5 is a flow chart illustrating a method for measuring perfusion according to one embodiment of the invention.

FIG. 5 illustrates a method for measuring perfusion according to some embodiments of the invention. Referring to FIG. 5, the detector captures frames associated with light intensity values 51 and sends those values to a processor 52. The light intensity values captured by the detector 51 are indicative of coherent light that was scattered by red blood cells as it transilluminated the finger. The coherent light transilluminating the finger renders an unfocused image, which is captured by the detector. The detector adequately samples the speckle pattern despite the unfocused image. Speckle sizes are increased by an opaque sheet with an aperture which alters the numerical aperture of the detector.

In some embodiments, the locations the locations of the coherent light source 13 and detector 11 are configured to couple to finger movement 15 via an enclosure 12. Accordingly, a patient's moving will cause the coherent light source 13 and detector 11 to move along with the patient's finger 15, according to some embodiments of the invention. Thus, the field of view of the tissue sample 15 remains constant upon movement of the tissue sample. Therefore, movement of the tissue sample 15 while measuring tissue perfusion does not alter the transmission geometry. The plurality of light intensity values received by the detector, therefore, remains constant upon movement of the tissue sample 15.

Based on the light intensity values associated with the unfocused image, the processor may compute speckle contrast spatially, temporally, or spatio-temporally (a hybrid of spatial and temporal) 53. To compute speckle contrast spatially, the processor may utilize a group of pixels at different spatial locations within the same frame. To compute speckle contrast temporally, the processor may utilize pixels from the same spatial location across a sequence of frames captured at different times. The processor may also compute speckle using a spatio-temporal method, which is a hybrid of the temporal and spatial methods.

Speckle contrast can be calculated as:

$$K = \frac{\sigma}{\langle I \rangle} \quad (1)$$

where K is contrast, σ is the standard deviation of a group of pixel values and <I> is the average of a group of pixel values.

Because some embodiments of the invention does not require a focused image, the invention may compute speckle contrast temporally from only 1 pixel location. Accordingly, the invention may use a photodiode as a detector. Photodiodes are cheaper than cameras with image-forming optics, which are required by existing LSI systems. Perfusion measurements acquired by utilizing only 1 pixel location are comparable in accuracy to those acquired by utilizing multiple pixel locations. In addition, perfusion measurements acquired by utilizing pixels from an unfocused image are comparable in accuracy to those acquired by laser Doppler, which is the gold standard in the field.

Figure 6:
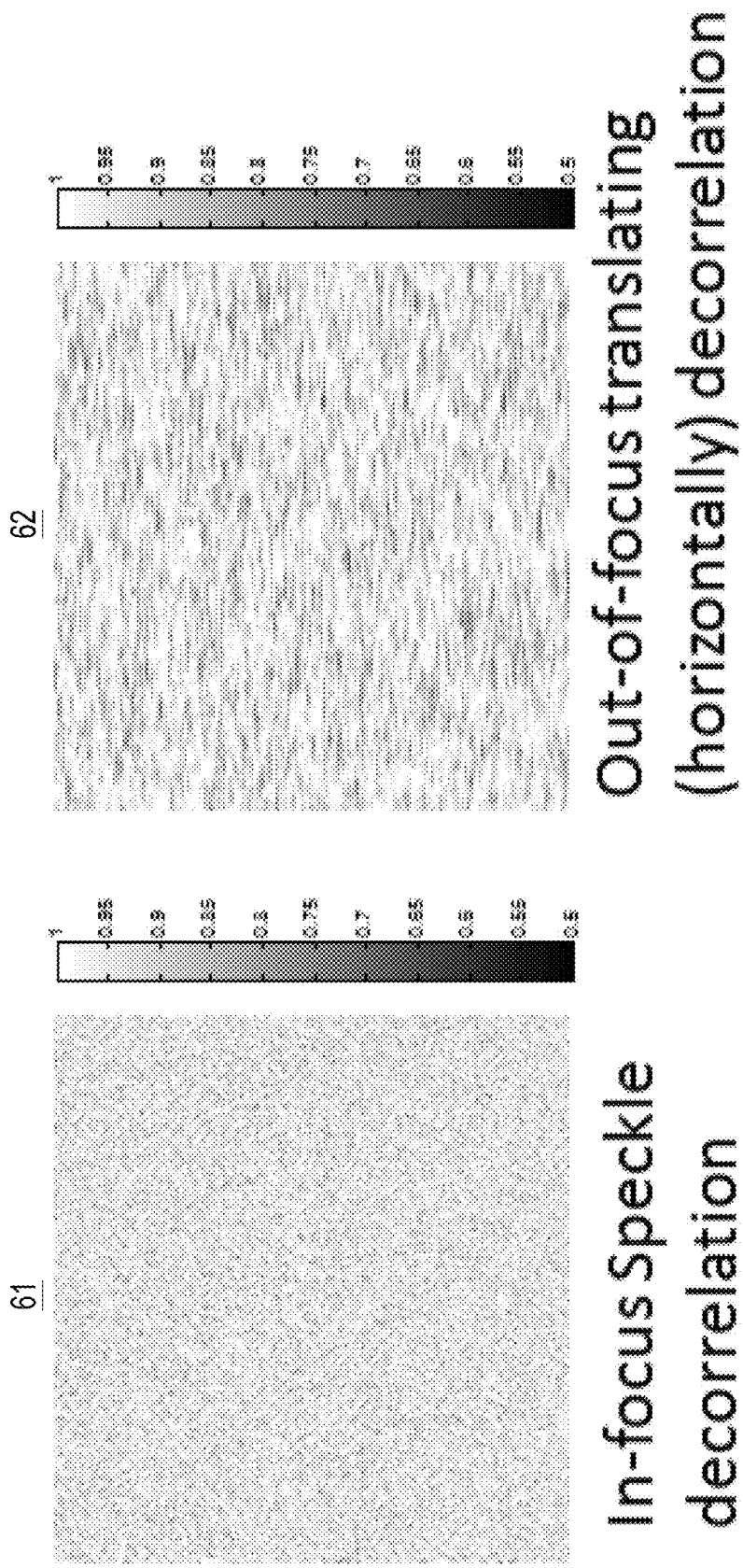
FIG. 6 illustrates streaking artifacts in in-focus and out-of-focus images.

The speckle contrast may also be computed using the standard deviation across the entire image. Doing so eliminates the artifacts in the "streaking images" that may otherwise result from using an unfocused image 62. Referring to FIG. 6, if the object being imaged is moved, the out of focus speckle pattern may translate. These artifacts may propogate to the speckle contrast image, creating "streaking images" 62. In-focus speckles do not translate, and thus the speckle contrast image does not exhibit the streaking images 61. The streaking in unfocused images 62 may be eliminated by calculating the standard deviation across the entire image. In addition, streaking is eliminated because of the random direction of motion of blood perfusion.

After calculating the speckle contrast value K, perfusion can be calculated as $$\text{Perfusion} = \frac{1}{K^2} \quad (2)$$

as suggested by Ramirez-San-Juan et al, although other factors may affect this computation, including camera exposure time, camera noise, optical absorption, and the presence of static scatterers.

Returning to FIG. 5, using equation (2), the processor may determine a metric of perfusion based on the computed speckle contrast value. In some embodiments of the invention, the processor determines a single metric of perfusion 54. The single metric of perfusion may be calculated by averaging a group of pixels or by any other suitable method. In some embodiments, the system does not display an image of perfusion. Rather, the system according to some embodiments displays a single metric of perfusion, which is more easily understood and processed by users. In some embodiments, the system optionally comprises a display. In some embodiments, the processor displays the single metric of perfusion on the display.

Figure 7:
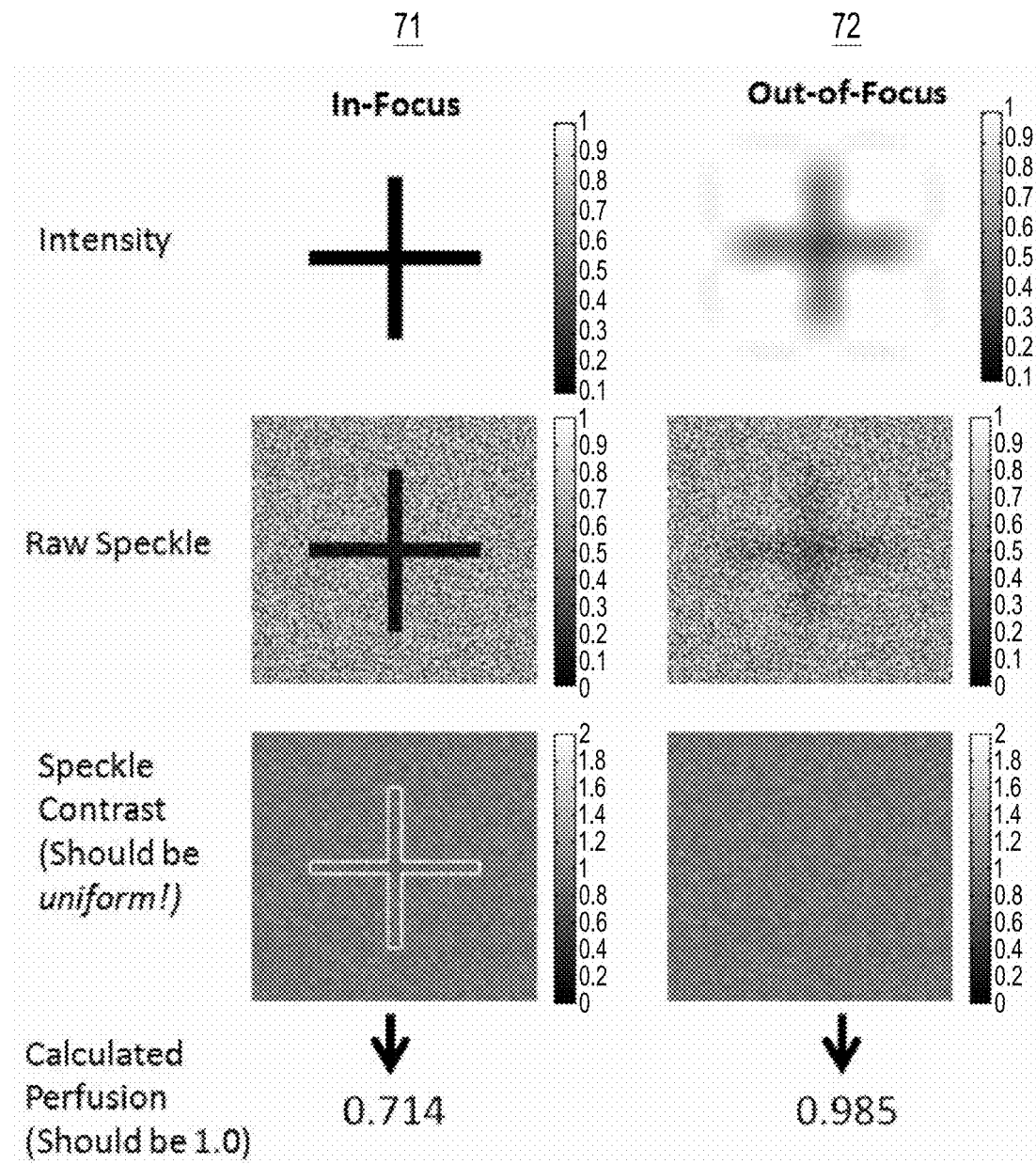
FIG. 7 illustrates inhomogeneities in in-focus and out-of-focus images.

As illustrated in FIG. 7, utilizing out-of-focus images can lead to more accurate data than in-focus images. The sharp intensity features of the inhomogeneities 71 with respect to in-focus images lead to an inflated standard deviation parameter (see equation (1)), thereby leading to an inaccurate speckle contrast value. Inhomogeneities may be caused by uneven illumination, absorption, optical properties, and/or scattering inhomogeneities in the tissue sample. Out-of-focus images are more robust to intensity inhomogeneities 72, leading to a more accurate speckle contrast value according to some embodiments of the invention.

Example 1

This example investigated whether the embodiment shown in FIGS. 4-*ab* ("the FIG. 4 embodiment") was capable of detecting perfusion changes in the ring finger 15 of a human subject during an arm cuff occlusion. For this experiment, the tip of the patient's ring finger 15 was illuminated using a single mode laser diode 13 (power of 90 mW, wavelength of 789 nm, Roithner LaserTechnik ADL-78901TL, Vienna, Austria). A laser diode driver (Thorlabs Inc. LDC200C, Newton, N.J.) was used to adjust the power output of the laser diode 13. A polydimethylsiloxane ("PDMS") cylinder 41 had been previously molded around a separate patient's finger. The thickness of the PDMS surrounding the patient's finger was approximately 3 mm. The distance between the finger 15 and laser 13 was 5 mm. The distance between the finger 15 and the detector 11 was 10 mm.

Light transmitted through the patient's ring finger 15 was then incident on an opaque sheet of aluminum cut into a circle 25 with a diameter of approximately 28 mm. At the center of the aluminum sheet 25 was an aperture approximately 1 mm in diameter. This opaque sheet 25 served to reduce the numerical aperture of the CCD camera used as a photodetector 11 (Point Grey Research FL2-08S2M-C, Richmond, BC). The aperture size was chosen such that the speckles within the speckle pattern incident on the detector 11 were at least two pixels in diameter as recommended by Kirkpatrick et al. to achieve adequate sampling. Data was transferred from the detector 11 to the computer using a 1393b cable 16.

The opaque aluminum sheet 25 was placed in direct contact with a linear polarizer sheet 26 (Thorlabs Inc. LPVISE2X2, Newton, N.J.). Like the aluminum sheet 25, the polarizer sheet 26 was also cut into a circle with a radius diameter of approximately 28 mm. Both of these parts 25, 26, were placed at the opening of the lens mount of the CCD camera 11.

No parts were used to form a focused image. For example, no lenses or mirrors were used to form a focused image. Therefore, the detector received an unfocused image. In addition, the distance between the laser, detector, and object were chosen to facilitate coupling, such that movement of the tissue sample 15 while measuring tissue perfusion would not alter the transmission geometry.

Data was acquired from the detector 11 using custom-written software written in the MATLAB coding language (Mathworks, Natick, Mass.). The exposure time was set at 5 ms and frames were acquired at 43 frames per second. Each frame was converted to speckle contrast values using equation (1) above. σ and <I> were computed at each pixel of each frame using a sliding window algorithm wherein the values to compute σ and <I> for each pixel are taken from the 7 by 7 neighborhood of pixels surrounding the pixel of interest. Pixels at the edge of the frame that did not have enough neighbors to complete a 7×7 neighborhood were ignored when computing a frame of K values.

Using equations (1) and (2) together allowed the computation of perfusion within the patient's finger 15 over time with a measurement frequency of 43 Hz. This measurement frequency was affected by both data transfer rates between the detector 11 and the computer used, the bit depth of the frames being analyzed (which was chosen to be 8-bit), and what fraction of pixels from the CCD camera 11 had their values transferred from CCD camera 11 to the computer. A 200 by 200 pixel region centered on the CCD camera 11 was chosen for this experiment as a compromise between signal to noise ratio and measurement frequency.

To perform an occlusion on the patient during perfusion measurement, an aneroid sphygmomanometer (Omron Health Care 108M, Lake Forest, Ill.) was placed on the upper arm of the limb being measured. The pressure applied to the upper arm using the aneroid sphygmomanometer was controlled by an individual who made pressure changes as quickly as possible.

Figure 8:
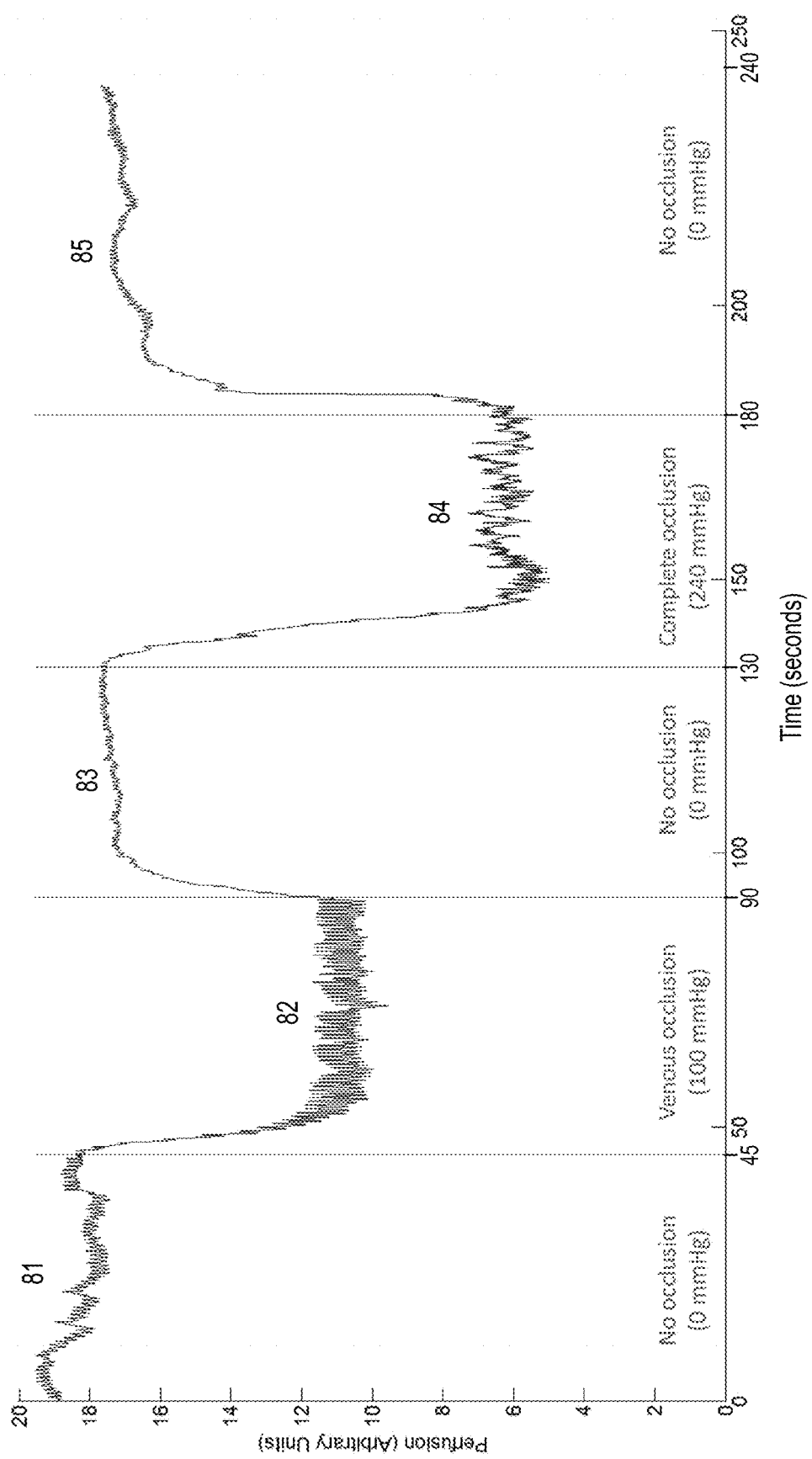
FIG. 8 is a graph illustrating perfusion data acquired from a human finger during intermittent arm cuff occlusion using the embodiment shown in FIGS. 4a-b.

During the experiment, perfusion in the patient's ring finger 15 was measured over a period of 240 seconds. The results of this experiment can be seen FIG. 8. During the first 45 seconds, the aneroid sphygmomanometer was at 0 mmHg, corresponding to no occlusion being applied. Thus, a baseline level of perfusion 81 is seen from 0-45 seconds. From 45 seconds to 90 seconds, the aneroid sphygmomanometer was pumped up to 100 mmHg, corresponding to a partial (venous only) occlusion. Thus, during partial occlusion from 45 to 90 seconds, a decrease in perfusion 82 can be seen. From 90 seconds to 130 seconds, the pressure in the aneroid sphygmomanometer was released back to 0 mmHg, corresponding to no occlusion. Thus, a return to baseline perfusion 83 can be observed from 90 seconds to 130 seconds. From 130 seconds to 180 seconds, the aneroid sphygmomanometer was pumped up to 240 mmHg, corresponding to a full (venous and arterial) occlusion. Thus, during full occlusion from 130 to 180 seconds, perfusion can be seen to decrease 84 even further as compared to the partial occlusion 82. From 180 seconds to 240 seconds, the pressure was released back to 0 mmHg, corresponding to no occlusion. Thus, a return to baseline perfusion 85 can be seen from 180 to 240 seconds.

The high frequency (ca. 0.75 Hz) perfusion oscillations can be attributed to the heart beat of the patient. Lower frequency oscillations are likely due to normal physiological changes in perfusion, possibly due to Mayer waves.

This experiment demonstrates in a human subject that changes in perfusion can be detected using the FIG. 4 embodiment. Further, the device 40 is also capable of detecting varying levels of perfusion. This includes both small fluctuations due to the heart beat, as well as much larger changes in perfusion such as when an occlusion is applied.

The FIG. 4 embodiment displayed accurate perfusion data, despite the small field of view (only a portion of a finger). Instead of displaying perfusion data as an image, the FIG. 4 embodiment displayed perfusion data as a single metric. Therefore, a large field of view was not necessary to accurately measure perfusion.

Figure 9:
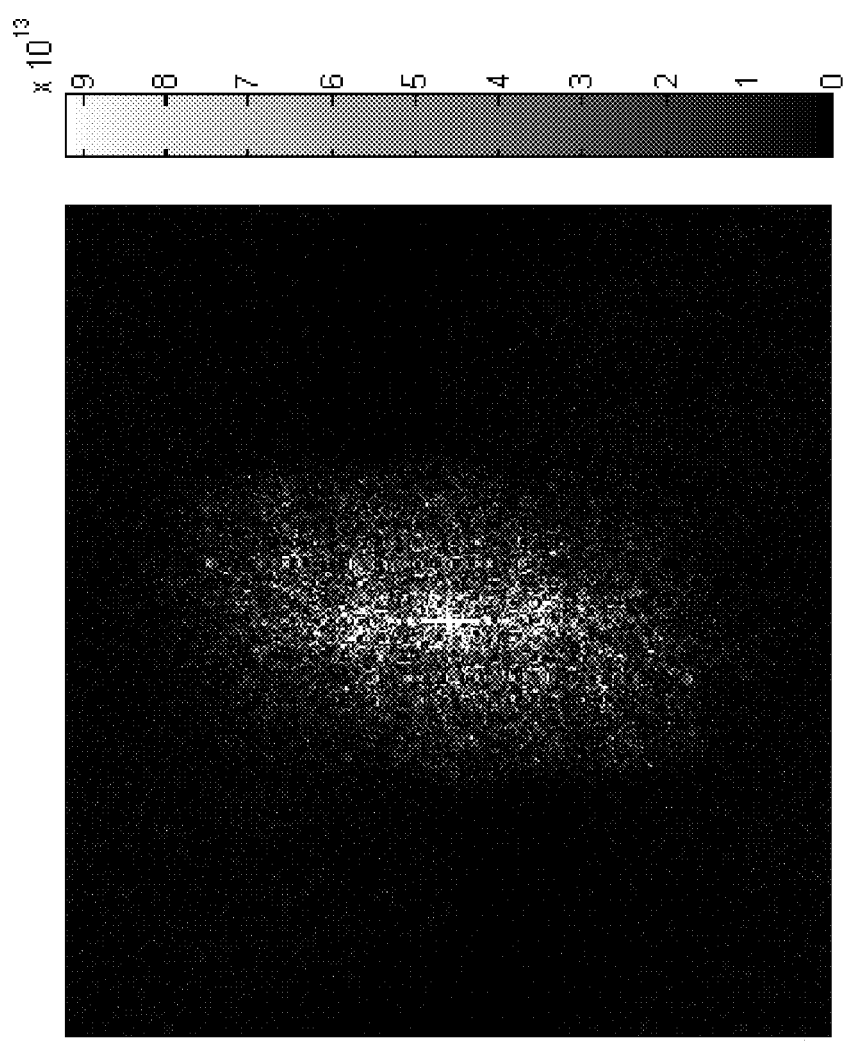
FIG. 9 illustrates the power spectral density of an image acquired using the embodiment shown in FIGS. 4a-b.

In addition, the FIG. 4 embodiment accurately measured perfusion despite the short distance between the laser, finger, and detector. Because of the short distance and the absence of lenses or mirrors, the FIG. 4 embodiment did not have a focal length. In other words, the FIG. 4 embodiment did not focus an image. The speckle size in unfocused images may be smaller than the speckle size in focused images. Therefore, the speckle pattern in unfocused images may be under-sampled by the detector 11, leading to erroneous data. FIG. 3 illustrates histograms of a properly sampled speckle pattern 31 and an under-sampled speckle pattern 32. As FIG. 3 illustrates, an under-sampled speckle pattern 32 can lead to erroneous data. Nevertheless, this experiment utilizing unfocused images produced accurate perfusion data. By using an opaque sheet with an aperture 25 near the detector 11, the numerical aperture of the detector 11 was altered, increasing the speckle size incident on the detector 11. Thus, the detector 11 properly sampled the speckle pattern, as illustrated by FIG. 9. FIG. 9 illustrates power spectral density of an image acquired using the FIG. 4 embodiment. As illustrated in FIG. 9, the vast majority of nonzero values of the power spectral density fall within the bounds of the map, demonstrating that the speckle pattern was properly sampled.

Figure 10:
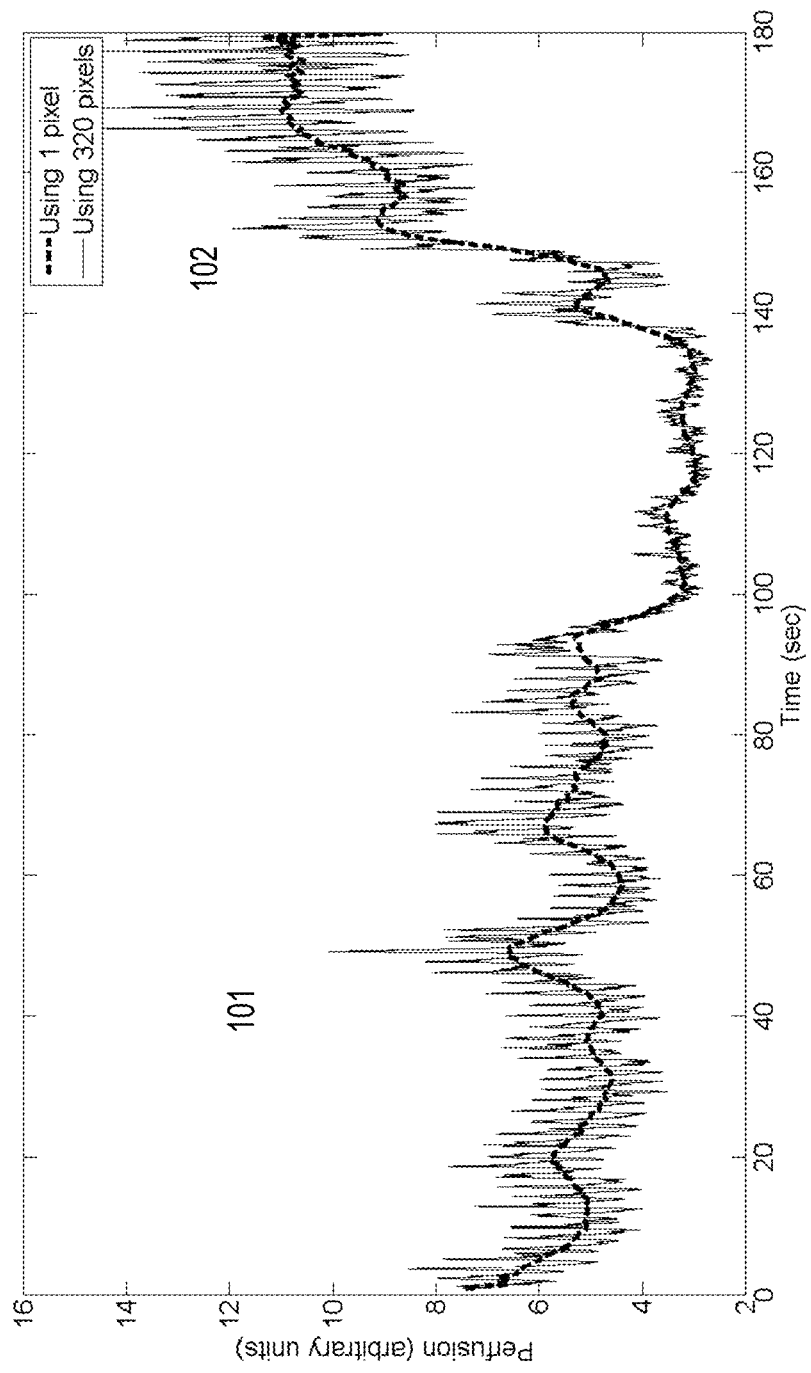
FIG. 10 illustrates perfusion data obtained using 1 pixel and 320 pixels.

Furthermore, as illustrated by FIG. 10, perfusion measurements using only 1 pixel are comparable in accuracy to those using a full image. FIG. 10 illustrates perfusion data acquired from a patient arm cuff occlusion using the FIG. 4 embodiment. Data was acquired using (1) only 1 pixel and (2) a full image, which contained 320 pixels. Arm cuff occlusion at 240 mmHg was applied 90 seconds into the experiment. Thus, a decrease in perfusion can be seen during this time period 101. The computed perfusion measurement from 1 pixel accurately follows the trend of the full image 101. The arm cuff occlusion was released 140 seconds into the experiment. Thus, perfusion can be seen to increase after 140 seconds 102. Again, the computed perfusion measurement from 1 pixel accurately follows the trend of the full image 102. (The high frequency oscillations displayed in the perfusion data computed from the full image reflect fluctuations in perfusion due to patient heartbeat.) This example demonstrates that accurate perfusion data may be obtained using only 1 pixel. Accordingly, a photodiode may be used as a detector. Photodiodes are cheaper than cameras with image-forming optics, which are required by existing LSI systems. In addition, this example demonstrates that accurate perfusion data may be obtained with an unfocused image.

Example 2

In this experiment, the FIG. 4 embodiment was used to measure perfusion from a phantom finger in place of a human finger. Blood vessels within the finger-simulating phantom were modeled via the inclusion of Tygon tubing (Norton Performance Plastics 720997, Akron, Ohio). The tubing was wound in a coil ca. 6 mm in diameter up the length of the whole phantom. The tubing has 0.050 inch inner diameter and a 0.090 inch outer diameter. The coiled tubing was covered in a layer PDMS that had been mixed with titanium oxide (Sigma Aldrich T8141-100G, St. Louis, Mo.) at a concentration of 0.74 mg/mL. This provided a PDMS solution with a reduced scattering coefficient of ca. 1 mm-1 at a wavelength of 789 nm. This reduced scattering coefficient was used because it is similar to that found in bulk human tissue.

To simulate blood flow in the phantom finger, defibrinated sheep blood (Quad Five 610, Ryegate, Mont.) was pumped through the coiled Tygon tubing. Blood was pumped using a peristaltic pump (APT instruments SP200V1.006, Rochester, Ill.). To mimic the pulsatile blood flow from a heart beat, two of the three rollers were removed from the peristaltic pump. This resulted in pulsatile flow with adjustable frequency but constant volumetric output with every pump. This is analogous to the human heart beating faster without any change in stroke volume.

The finger-simulating phantom was placed in the finger cavity 41 of the FIG. 4 embodiment. Using the same settings as in EXAMPLE 1, perfusion was measured from the finger-simulating phantom. Data was collected for a total of 60 seconds. This data was converted to a metric of perfusion in the same manner described in EXAMPLE 1. During the first 30 seconds of measurement, the pump was set at frequency volumetric output of 0.67 mL/min. After 30 seconds, the frequency of the pump was adjusted so that the volumetric output was 2.9 mL/min. The finger-simulating phantom was measured at this higher frequency for 30 seconds. The collected data can be seen in FIG. 11. As the frequency of the pump increased (after 30 seconds), the volume of blood moving through the finger-simulating phantom for a given amount of time increased 111. Thus, the measured perfusion increased when the volumetric output was increased from 0.67 mL/min to 2.9 mL/min.

Only the pump frequency, and not the volumetric output at each pump, was altered in this experiment. Therefore, perfusion metrics that do not depend on pump frequency, such as plethysmographic waveform amplitude, would not have detected a change in perfusion in this experiment. To illustrate this point, a pulse oximeter commonly used in clinical situations (Masimo Radical-7, Irvine, Calif.), which provides a perfusion index based on amplitude changes in the plethysmographic waveform, was used to acquire data on the same finger-simulating phantom. Data was acquired from the finger-simulating phantom for 60 seconds. After the first 30 seconds of measurement, the frequency of the pump was increased so that the volumetric output was increased from 0.67 mL/min to 2.9 mL/min.

Figure 12:
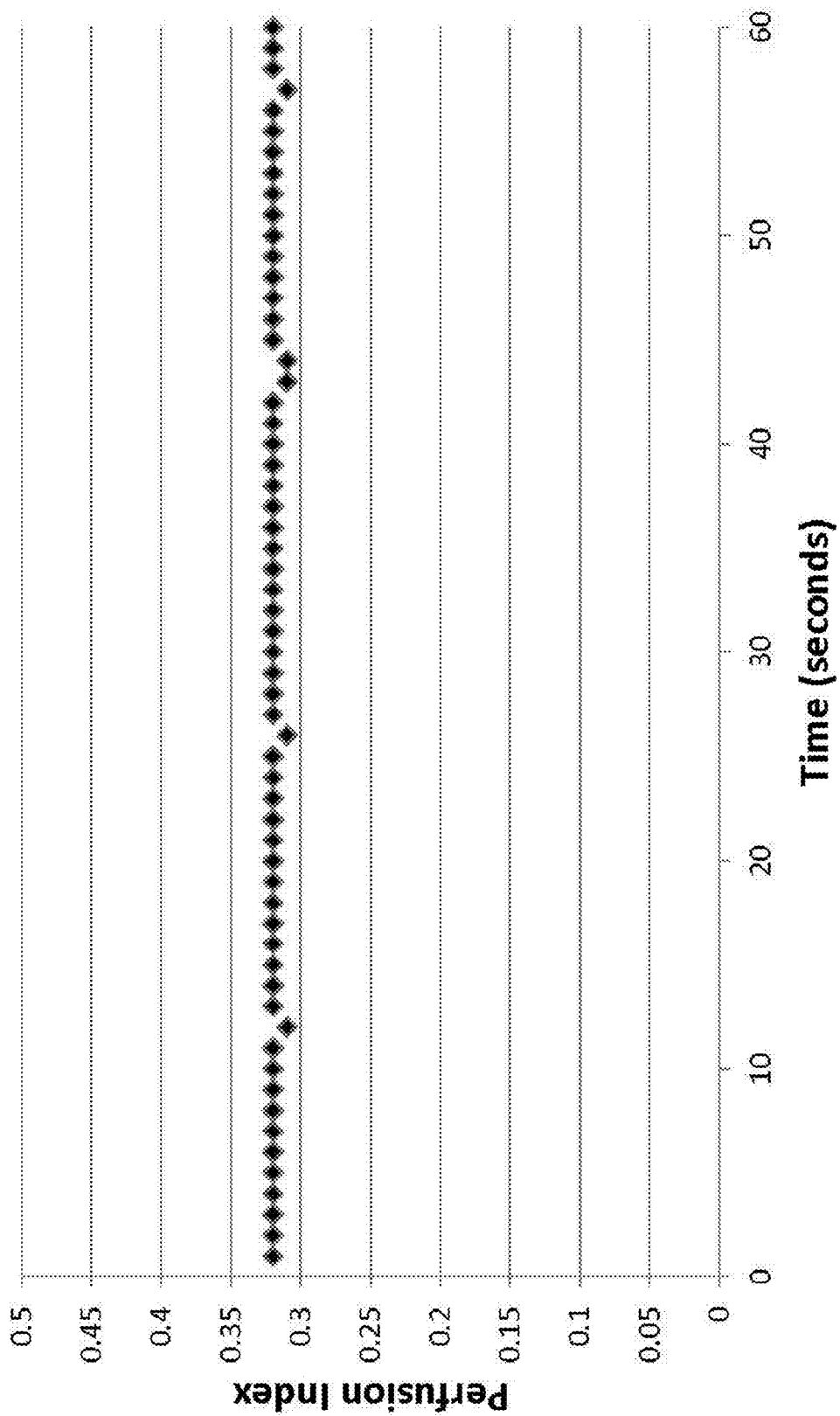
FIG. 12 is a graph illustrating perfusion data acquired from a finger-simulating phantom using a pulse oximeter.

The results are illustrated in FIG. 12. As seen in FIG. 12, the pulse oximeter is capable of computing a perfusion index. However, it erroneously fails to detect any change in perfusion index when the volumetric output frequency of the pump is increased.

Example 3

The purpose of this experiment was to compare perfusion measurements made using some embodiments of the invention and a laser Doppler flowmetry system (Perimed PeriFlux System 5000, Ardmore, Pa.). Laser Doppler flowmetry was chosen for this comparison because it is very commonly used in the clinic to assess perfusion and is considered a gold standard for doing so. Such assessment is thought to be prognostic of wound healing, flap monitoring, ulcer health, and others.

In this experiment, the phantom finger described in EXAMPLE 2 was used in place of a patient's finger. The apparatus used to measure perfusion was the same embodiment illustrated in FIGS. 4a-b, except the PDMS finger cavity 41 was removed ("Example 3 embodiment"). A pulsatile pump (LMI Unidose U12-281, FL) was used to pump a 1% solution of Intralipid (Baxter Healthcare Corporation NDC 0338-0519-03, Deerfield, Ill.) diluted with water through the length of tubing. This concentration of Intralipid was used because it had a scattering coefficient similar to that of human tissue within the visible and near infrared optical spectrum. A portion of the length of tubing was placed where the finger cavity 41 was located so that optical assessment of flow within a portion of the tubing could be performed. Care was taken to assure that the center of the tubing was at an equal height compared to the diode laser 13 and detector 11. Data was collected using the same settings as in EXAMPLE 1 and collected data was converted to perfusion in the same manner as in EXAMPLE 1.

At a separate portion of the same length of tubing, the detection probe from the laser Doppler flowmeter was affixed to the tubing using double-sided tape. Care was taken so that both the laser Doppler flowmeter and the FIG. 3 embodiment acquired data from straight portions of the tubing. Although the FIG. 3 embodiment and the laser Doppler flowmeter measured perfusion at different locations on the tubing, it was assumed that flow within both locations on the tubing would be nearly identical. This is a valid assumption given the flow of a non-compressible fluid (water) through a uniform tube.

Figure 14:
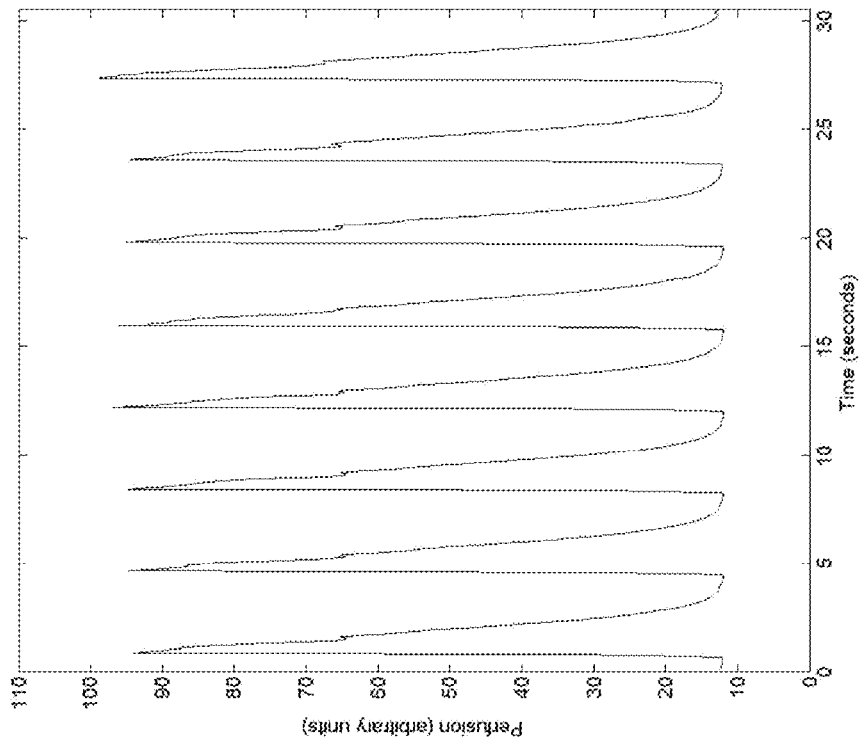
FIG. 14 is a graph illustrating perfusion data acquired from a finger-simulating phantom with pulsatile blood flow using one embodiment of the invention.
Figure 13:
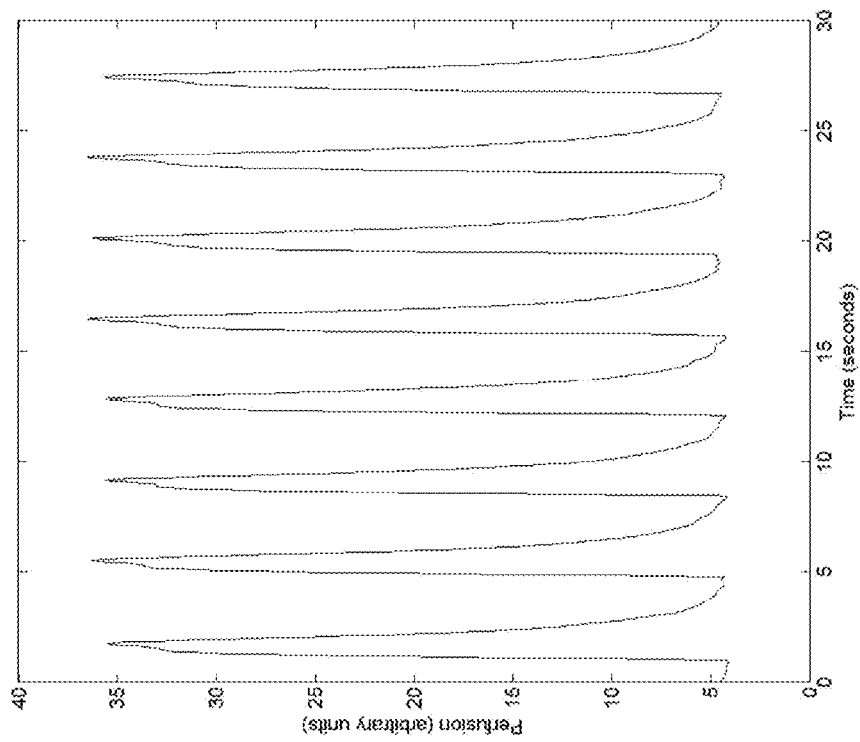
FIG. 13 is a graph illustrating perfusion data acquired from a finger-simulating phantom with pulsatile blood flow using a laser Doppler flowmetry system.

The pulsatile pump was set to a pump frequency of 0.3 Hz and 80% of the maximum stroke volume. While Intralipid was being pumped, perfusion data was collected from the laser Doppler flowmeter and the Example 3 embodiment for 30 seconds. The acquired perfusion data can be seen in FIGS. 13-14. The two plots within FIGS. 13-14 were acquired simultaneously and demonstrate the pulsatile fluctuations in perfusion detected during pulsatile pumping. The perfusion data from the laser Doppler flowmeter, shown in FIG. 13, follows a nearly identical trend as that from the Example 3 embodiment, shown in FIG. 14. Thus, this example demonstrates that the Example 3 embodiment provides data comparable to the gold standard used for clinical perfusion measurements.

The change in signal amplitude during each stroke from the pump was higher using the Example 3 embodiment compared to the laser Doppler flowmeter. However, this is likely due to the limited sampling volume of the laser Doppler flowmeter. This limited sampling volume results from the fact that the laser Doppler flowmeter probes functions in a reflection geometry, and as such, has been suggested to only interrogate ~1 mm deep into objects with similar scattering properties to tissue (such as the 1% Intralipid solution used in this experiment). In contrast, the Example 3 embodiment was configured to interrogate the full thickness of the tube due to its use of transmission geometry. As such, a portion of the detected photons would interact with scattering particles near the center of the tube.

Figure 11:
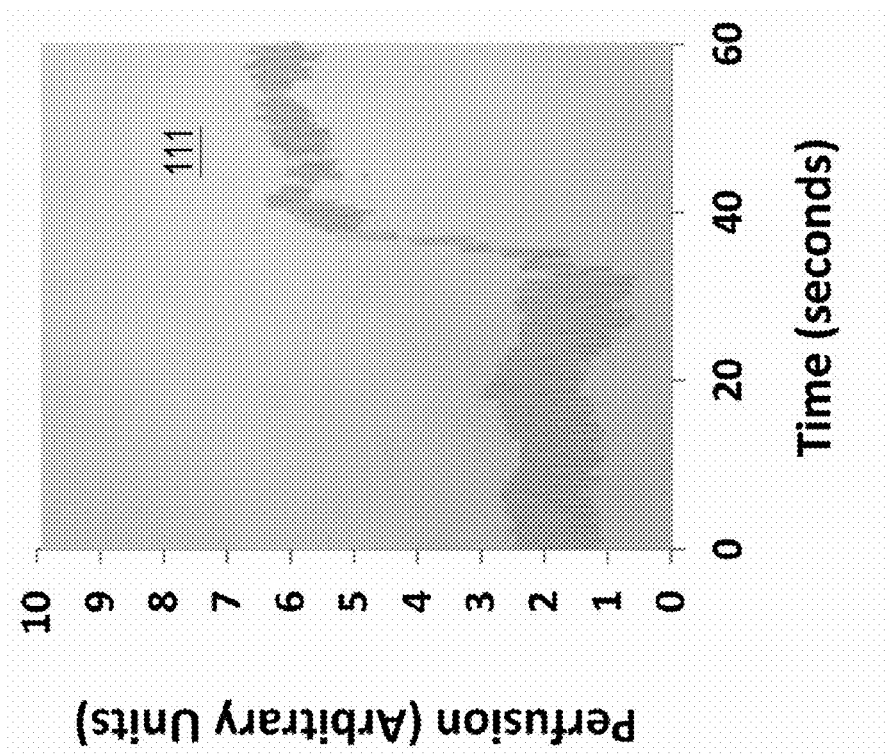
FIG. 11 is a graph illustrating perfusion data acquired from a finger-simulating phantom using the embodiment shown in FIGS. 4a-b.

Assuming laminar or quasi-laminar flow within the tube, fluid in the center of the tube moved faster than fluid at the periphery. The Example 3 embodiment was configured to interrogate the full thickness of the tube (and fluid in the center of the tube), while Doppler flowmeter only interrogates ~1 mm deep (the periphery of the tube). Thus, the amplitude from the Example 3 embodiment is higher than the amplitude of the Laser Doppler flowmeter. As a result, the Example 3 embodiment would detect a greater degree of change in perfusion as compared to the laser Doppler flowmeter, as illustrated by FIGS. 11-12.

This example demonstrates that the Example 3 embodiment measures accurate perfusion data comparable to the gold standard in the field, laser Doppler flowmeter. Despite the unfocused image and reduced field of view, some embodiments of the invention measure accurate perfusion data.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

REFERENCES (HEREIN INCORPORATED BY REFERENCE)

1. [S. J. Kirkpatrick, D. D. Duncan, and E. M. Wells-Gray, "detrimental effects of speckle-pixel size matching in laser speckle contrast imaging," Opt. Lett. 33, 2886-2888 (2008).
2. Jakobsson, A. & Nilsson, G. E. Prediction of sampling depth and photon pathlength in laser Doppler flowmetry. Medical and biological Engineering and Computing 31, 301-307 (1993).
3. [Flock, S. T., Jacques, S. L., Wilson, B. C., Star, W. M. & van Gemert, M. J. C. Optical properties of intralipid: A phantom medium for light propagation studies. Lasers in Surgery and Medicine 12, 510-519, doi:10.1002/lsm.1900120510 (1992).
4. Cannesson, M. et al. Does the Pleth variability index indicate the respiratory-induced variation in the plethysmogram and arterial pressure waveforms? Anesthesia & Analgesia 106, 1189-1194 (2008).
5. Killip Iii, T. Oscillation of blood flow and vascular resistance during Mayer waves. Circulation research 11, 987-993 (1962).
6. Ramirez-San-Juan, J. C., Ramos-Garcia, R., Guizar-Iturbide, I., Martinez-Niconoff, G. & Choi, B. Impact of velocity distribution assumption on simplified laser speckle imaging equation. Opt Express 16, 3197-3202, doi:10.1364/OE.16.003197 (2008).
7. Fercher, A. F. & Briers, J. D. Flow visualization by means of single-exposure speckle photography. Opt Commun 37, 326-330, doi:10.1016/0030-4018(81)90428-4 (1981).
8. Kirkpatrick, S. J., Duncan, D. D. & Wells-Gray, E. M. Detrimental effects of speckle-pixel size matching in laser speckle contrast imaging. J Biomed Opt 33, 2886-2888, doi:doi:10.1364/OL.33.002886 (2008).
9. Boas, D. A. & Dunn, A. K. Laser speckle contrast imaging in biomedical optics. J Biomed Opt 15, doi:doi:10.1117/1.3285504 (2010).
10. Choi, B., Ramirez-San-Juan, J. C., Lotfi, J. & Nelson, J. S. Linear response range characterization and in vivo application of laser speckle imaging of blood flow dynamics. J Biomed Opt 11, doi:10.1117/1.2341196 (2006).
11. Yuan, S., Devor, A., Boas, D. A. & Dunn, A. K. Determination of optimal exposure time for imaging of blood flow changes with laser speckle contrast imaging. Appl Optics 44, 1823-1830, doi:doi:10.1364/AO.44.001823 (2005).
12. White, S. M., George, S. C. & Choi, B. Automated computation of functional vascular density using laser speckle imaging in a rodent window chamber model. Microvas Res 82, 92-95, doi:10.1016/j.mvr.2011.03.006 (2011).
13. Qiu, J. et al. Spatiotemporal laser speckle contrast analysis for blood flow imaging with maximized speckle contrast. Journal of Biomedical Optics 15, 016003-016003 (2010).

What is claimed is:

1. An apparatus comprising:
a coherent light source configured to illuminate a tissue sample;
a digital camera sensor comprising a plurality of light-sensitive elements configured to capture a plurality of light intensity values;
an enclosure configured to accommodate the tissue sample, the enclosure being coupled to the coherent light source and the digital camera sensor, wherein the enclosure is configured to position the coherent light source no more than 5 mm from the tissue sample and to position the digital camera sensor no more than 10 mm from the tissue sample, wherein the enclosure is configured to position the coherent light source and the digital camera sensor on opposing sides of the tissue sample; and
a processor,
wherein the enclosure is configured to be affixed to the tissue sample such that the enclosure cannot move independently from the tissue sample,
wherein the digital camera sensor is configured to transfer the plurality of light intensity values to the processor, and
wherein the processor is configured to:
determine an average of at least some light intensity values of the plurality of light intensity values; and
compute, based on at least the average, a speckle contrast parameter indicative of tissue perfusion in the tissue sample.

2. The apparatus of claim 1, wherein the enclosure is configured to position the light source and the digital camera sensor in a transmission geometry with respect to the tissue sample.

3. The apparatus of claim 1, wherein the enclosure is configured to position at least one of: the light source in direct contact with the tissue sample, or the digital camera sensor in direct contact with the tissue sample.

4. The apparatus of claim 1, wherein the tissue sample is a soft tissue perfused with blood vessels.

5. The apparatus of claim 4, wherein the tissue sample is a digit, an earlobe, or a nostril.

6. The apparatus of claim 1, wherein the digital camera sensor comprises image-forming optics which have a front focal distance and wherein the enclosure is configured to position the image-forming optics a distance from the tissue sample not equal to the front focal distance.

7. The apparatus of claim 1, wherein the enclosure is configured to position the digital camera sensor a fixed distance from the tissue sample and the apparatus is configured so that the digital camera sensor captures light from a fixed field of view.

8. The apparatus of claim 7, wherein the fixed field of view is configured to capture light from only a portion of the tissue sample.

9. The apparatus of claim 8, wherein the fixed field of view is sized to enable the processor to determine the speckle contrast parameter without mapping areas of relatively high blood flow and areas of relatively low blood flow in the tissue sample within a single image.

10. The apparatus of claim 8, wherein the apparatus is configured to achieve a pixel to speckle size ratio of at least 2:1.

11. The apparatus of claim 1, wherein the digital camera sensor comprises more than two pixels.

12. The apparatus of claim 1, wherein the speckle contrast parameter is defined as a standard deviation of the at least some of the light intensity values divided by the average of the at least some of the light intensity values.

13. The apparatus of claim 1, wherein the enclosure comprises a space for receiving the tissue sample, the space being no larger than a space configured to receive a human digit.

14. The apparatus of claim 1, further comprising an opaque sheet having an aperture positioned in front of the digital camera sensor such that the aperture is configured to be positioned between the digital camera sensor and the tissue sample.

15. The apparatus of claim 14, wherein the opaque sheet is configured to be placed against the tissue sample by the enclosure without any separation distance between the tissue sample and the opaque sheet.

16. The apparatus of claim 14, wherein the opaque sheet is configured to be placed less than 10 mm from the digital camera sensor.

17. The apparatus of claim 14, wherein the aperture is 1 mm in diameter.

18. The apparatus of claim 1, wherein the apparatus is sufficiently compact enough to be freely supported by a single human finger.

19. The apparatus of claim 1, wherein the processor is configured to determine, based on the speckle contrast parameter, a metric of the tissue perfusion in the tissue sample.

20. A method of determining a speckle contrast parameter indicative of perfusion in a soft tissue sample, the method comprising:
placing a soft tissue sample perfused with blood vessels within an enclosure of an apparatus, the apparatus comprising:
a coherent light source configured to illuminate the soft tissue sample; and
a digital camera sensor comprising a plurality of light-sensitive elements configured to capture a plurality of light intensity values from the soft tissue sample and configured to transfer the plurality of light intensity values to a processor,
wherein the enclosure is coupled to the coherent light source and the digital camera sensor and fixes the coherent light source and the digital camera sensor in a fixed spatial relationship with respect to the soft tissue sample such that neither can move independently of the soft tissue sample or independently of the other during use, wherein the enclosure is configured to position the coherent light source no more than 5 mm from the soft tissue sample and to position the digital camera sensor no more than 10 mm from the soft tissue sample, wherein the enclosure is configured to position the coherent light source and the digital camera sensor on opposing sides of the soft tissue sample, and
wherein the apparatus is configured such that the digital camera sensor captures a fixed field of view of a portion of the soft tissue sample;
illuminating the soft tissue sample with the coherent light source;
capturing with the digital camera sensor an image from the fixed field of view comprising the plurality of light intensity values;
determining, with the processor, an average of at least some light intensity values of the plurality of light intensity values; and
computing, with the processor, the speckle contrast parameter indicative of tissue perfusion in the tissue sample based on at least the average.

21. The method of claim 20, wherein the captured image is an unfocused image.

22. The method of claim 20, wherein computing the speckle contrast parameter comprises computing the speckle contrast parameter without mapping blood flow within the soft tissue sample.

23. The method of claim 20, further comprising calculating, with the processor, a metric of perfusion directly from the speckle contrast parameter.

* * * * *